(12) United States Patent
Feinbloom et al.

(10) Patent No.: US 10,247,384 B1
(45) Date of Patent: Apr. 2, 2019

(54) LED LIGHTING ELEMENT AND METHOD OF MANUFACTURING SAME

(71) Applicant: Designs for Vision, Inc., Bohemia, NY (US)

(72) Inventors: Richard E. Feinbloom, New York, NY (US); Kenneth N. Braganca, Sayville, NY (US); Matthew Kenyon, St. James, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 15/921,217

(22) Filed: Mar. 14, 2018

Related U.S. Application Data

(60) Provisional application No. 62/561,125, filed on Sep. 20, 2017, provisional application No. 62/502,602, filed on May 6, 2017.

(51) Int. Cl.
*F21V 5/00* (2018.01)
*F21V 5/04* (2006.01)
*H05K 1/02* (2006.01)
*H05K 1/18* (2006.01)
*F21V 15/01* (2006.01)
(Continued)

(52) U.S. Cl.
CPC ............... *F21V 5/008* (2013.01); *F21V 5/04* (2013.01); *F21V 15/01* (2013.01); *F21V 17/12* (2013.01); *F21V 23/005* (2013.01); *H05K 1/181* (2013.01); *F21V 29/503* (2015.01); *F21V 29/70* (2015.01); *F21W 2131/20* (2013.01); *F21W 2131/202* (2013.01); *F21W 2131/205* (2013.01); *F21W 2131/208* (2013.01); *F21Y 2115/10* (2016.08); *H05K 1/0203* (2013.01); *H05K 2201/09027* (2013.01); *H05K 2201/10106* (2013.01); *H05K 2201/10121* (2013.01)

(58) Field of Classification Search
CPC ......... F21W 2131/20; F21W 2131/202; F21W 2131/205; F21W 2131/208; F21V 21/084; F21V 5/008; A61B 90/30; A61B 90/35; A61B 2090/309; A61B 2090/502; A61C 1/088
See application file for complete search history.

(56) References Cited

U.S. PATENT DOCUMENTS 6,461,024 B1 * 10/2002 Becker .................... F21V 5/008
362/331
7,690,806 B2 4/2010 Feinbloom
(Continued)

FOREIGN PATENT DOCUMENTS

CA 2789607 A1 * 8/2011 ............. F21S 6/003

*Primary Examiner* — Alexander K Garlen
*Assistant Examiner* — Colin J Cattanach
(74) *Attorney, Agent, or Firm* — Law Office of Carl Giordano, PC

(57) ABSTRACT

A lighting element is disclosed that provides a projection of light forming a substantially uniform bright light on a surface a known distance from the lighting element. The lighting elements includes a dome lens that is removably positioned on a light source, such that the light source is retained at a location within a focal length of a projection lens and at or within a focal length of the dome lens. The dome lens magnifies the light outputted by the light source, such that the projected light is brighter than the light generated by the light source.

19 Claims, 18 Drawing Sheets

(51) Int. Cl.
*F21V 17/12* (2006.01)
*F21V 23/00* (2015.01)
*F21V 29/70* (2015.01)
*F21V 29/503* (2015.01)
*F21Y 115/10* (2016.01)
*F21W 131/20* (2006.01)
*F21W 131/202* (2006.01)
*F21W 131/205* (2006.01)
*F21W 131/208* (2006.01)

(56) References Cited

U.S. PATENT DOCUMENTS

| | | | |
|---|---|---|---|
| 8,215,791 B2 | 7/2012 | Feinbloom | |
| RE46,463 E | 7/2017 | Feinbloom | |
| 9,791,138 B1 | 10/2017 | Feinbloom | |
| 2008/0019011 A1* | 1/2008 | Krneta | G02B 7/023 359/641 |
| 2012/0120635 A1* | 5/2012 | Strong | F21V 21/084 362/105 |
| 2013/0301242 A1* | 11/2013 | Sharrah | F21V 21/084 362/105 |
| 2014/0293588 A1* | 10/2014 | Chang | F21V 21/084 362/103 |
| 2014/0334157 A1* | 11/2014 | Ferguson | F21V 21/084 362/277 |
| 2014/0334159 A1* | 11/2014 | Ferguson | A61B 90/35 362/311.02 |
| 2016/0123563 A1* | 5/2016 | Ferguson | F21V 21/084 362/277 |
| 2017/0159917 A1* | 6/2017 | Oren | A61B 90/35 |

* cited by examiner

FIG. 6
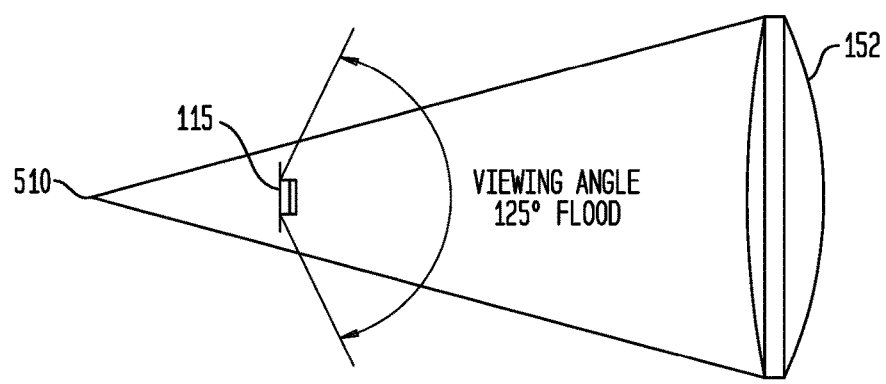
FIG. 7
FIG. 7
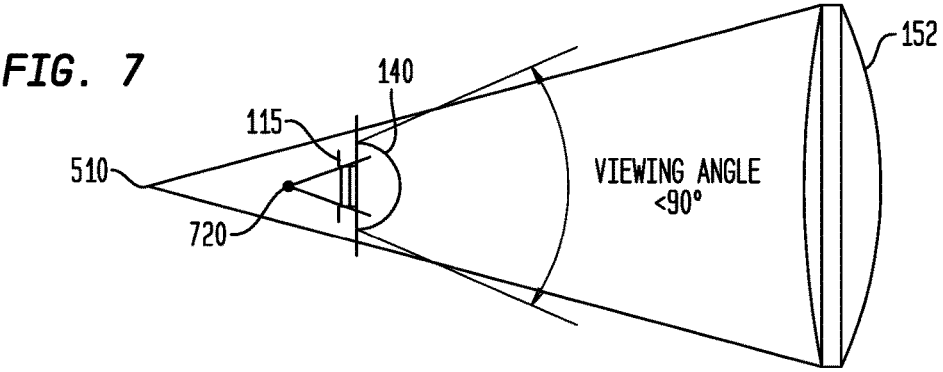

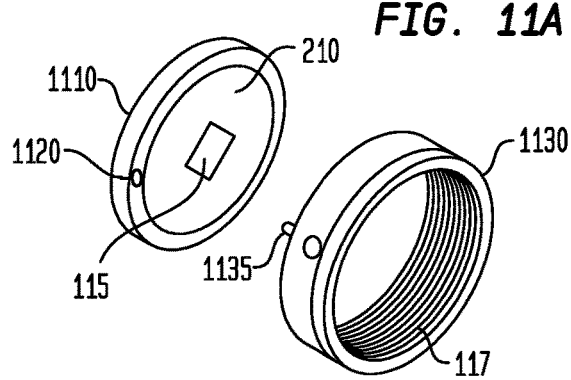
FIG. 11A
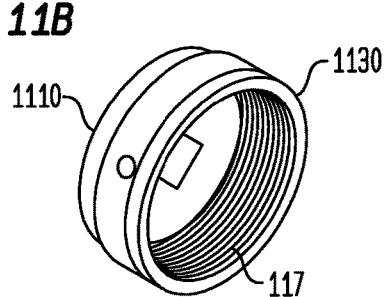
FIG. 11B
FIG. 11C
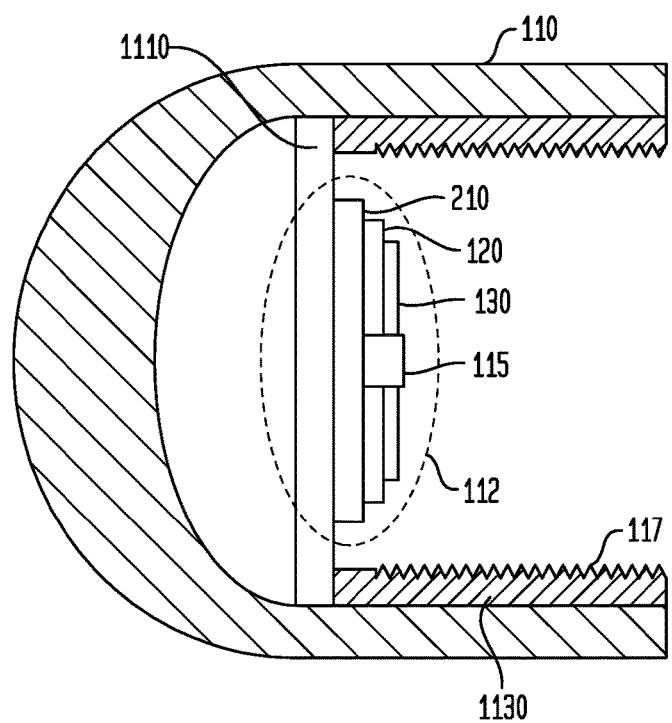

LED LIGHTING ELEMENT AND METHOD OF MANUFACTURING SAME

CLAIM OF PRIORITY

This application claims priority to, and the benefit of the earlier filing date of provisional applications Ser. No. 62/561,125 filed on Sep. 20, 2017 and 62/502,605 62/502,602 filed on May 6, 2017, the contents of all of which are incorporated by reference, herein.

RELATED APPLICATIONS

This application is related to the teaching of U.S. Pat. Nos. 7,690,806, 8,215,791, RE46463, and 9,791,138, which are assigned to the same Assignee as that of the instant application, and whose contents are incorporated by reference, herein.

FIELD OF THE INVENTION

The instant application relates to the field of optics and more particularly to a lighting element and light assembly having increased illumination output.

BACKGROUND OF THE INVENTION

Professionals, such as operating room doctors, surgeons, dentists, hygienists, EMT, mechanics, etc., require light to provide adequate illumination to the operating field. Having this light coming from the point of view of the user allows for shadow-free operation. The technology for providing the medical field, for example, this illumination is dominated by battery powered headlights and overhead lighting that allow the user to direct a light output onto a surface the user is looking at.

In addition, it is advantageous for the light that is projected onto the surface be as uniformly distributed as possible.

Light emitting diodes (LEDs) are becoming a predominate source of light, as they are light-weight, require less power, and provide a whiter light than conventional incandescent or halogen lights. However, newer generation LED technology provides for smaller LED packaging, which in turn reduces the light output of each LED. That is, as the efficiency of LED technology has increased, LED die are continually being made smaller. However, this smaller size makes the total light output of the LED (or LED package) to be less than that of conventional LEDs.

To compensate for the reduced size (and reduced output), generally the number of LEDs included within a light package that operates as a light source need to be increased to provide a projected light size that is comparable to the older LED technology. However, the increased number of required LEDs causes the projected light to be displayed to show the increased number of LED images. In addition, as it is known in the art, LED light output is dependent upon a current (or voltage) applied to the LED. To increase the brightness of newer generation of LEDs, an increase in the current applied to the new generation LEDs is necessary. However, as the current output of the battery is increased, the duration of the usable output decreases.

Hence, there is a need in the industry for a light assembly that provides a substantially uniform bright light on a surface without increasing the current to the LED, which reduces the life expectancy of the device.

SUMMARY OF THE INVENTION

A lighting element (or device) for providing an increased output illumination without the need for an increased power (voltage/current) input is disclosed.

A method for manufacturing a lighting element providing an increased output illumination without the need for an increased power output is disclosed.

In one aspect of the invention, an LED (or LED array) is positioned within or at the focal length of a short focal length dome magnifier and concurrently within a focal length of a longer length magnification lens, such that the projection of the light from the LED (or LED array) is substantially uniform.

In one aspect of the invention, an aperture may be incorporated between the dome magnifier and the LED such that stray light is avoided in the projected light.

In one aspect of the invention, a method for positioning the LED within the focal length of the dome magnifier is disclosed.

In one aspect of the invention, a heat sink is incorporated into a housing of the device to remove heat generated by the LED (or the LED array).

In one aspect of the invention, the dome magnifier is proximate to, or in contact with, the LED (or LED array) without the use of adhesive materials. The non-use of adhesive materials is advantageous as it prevents lens fogging due to any out-gassing of the heated adhesive material.

In accordance with the principles of the invention, a lighting element with an increased illumination output may be incorporated into a self-contained, battery operated, lighting unit.

In accordance with the principles of the invention, a light assembly including a lighting element having an increased illumination intensity may be attached to an eyewear, a headband or a head-strap to provide a substantially uniform light on a plane that the eye is focused on.

In accordance with the principles of the invention, a light assembly including a lighting element having an increased illumination intensity may be incorporated into a stand-alone device, such as an overhead lamp, a table lamp, a flashlight, and similar lighting devices, wherein a substantially uniform light is projected onto a surface.

BRIEF DESCRIPTION OF THE FIGURES

For a better understanding of exemplary embodiments and to show how the same may be carried into effect, reference is made to the accompanying drawings. It is stressed that the illustrative embodiments shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 6 illustrates a side view of an exemplary lighting configuration using older technology LED.

FIG. 7 illustrates a side view of an exemplary lighting configuration in accordance with the principles of the invention.

FIG. 11A illustrates an exploded perspective view of an exemplary PCB/LED assembly and threaded section in accordance with the principles of the invention.

FIG. 11B illustrates a perspective view of the exemplary PCB/LED assembly shown in FIG. 11A.

FIG. 11C illustrates a cross-section view of another aspect of a lighting element in accordance with the principles of the invention.

It is to be understood that the figures and descriptions of the present invention described herein have been simplified to illustrate the elements that are relevant for a clear understanding of the present invention, while eliminating, for purposes of clarity many other elements. However, because these omitted elements are well-known in the art, and because they do not facilitate a better understanding of the present invention, a discussion of such element is not provided herein. The disclosure herein is directed to also variations and modifications known or should be known to those skilled in the art from a reading the disclosure presented herein.

DETAILED DESCRIPTION

Figure 1:
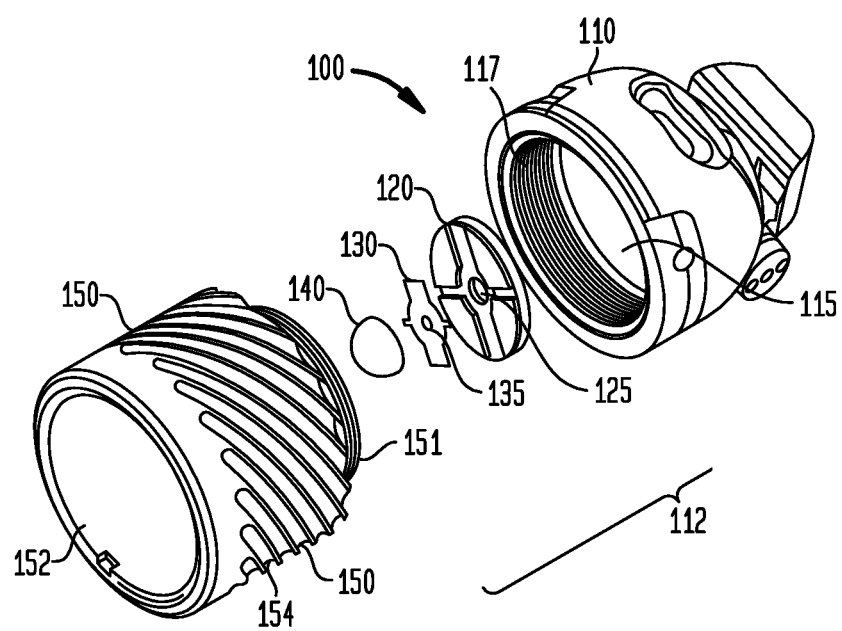
FIG. 1 illustrates a perspective view of a light assembly in accordance with the principles of the invention.

FIG. 1 illustrates an exploded prospective view of a light assembly 100 in accordance with the principles of the invention.

The light assembly 100 comprises a housing 110 including therein a lighting element 112 comprising a Light Emitting Diode (LED) 115 substantially centered on a printed circuit board (not shown) that is retained within the housing 110. The printed circuit board (PCB) includes electrical/electronic circuitry that controls the operation of LED 115 (e.g., turn on/off). An aperture holder (or plate) 120 and aperture 130, including substantially centered openings 125, 135 respectfully, are further illustrated. Aperture holder 120 and aperture 130, as will be discussed, provide for reduction of stray light emanating from LED 115.

Although described herein is the term "LED", it would be under stood that the term "LED," may comprise a plurality of LEDs arranged in a pattern (e.g., a matrix). Hence, the use of the term "LED," refers to at least one LED.

Further illustrated is a dome lens 140 that is substantially centered over LED 115. As will be discussed, LED 115 is positioned within or at a focal point of dome lens 140.

A lens assembly 150 is further illustrated and is attachable to housing 110 to retain the lighting element 112 within the housing 110.

Housing 110, further includes an internal screw thread 117, which mates to a corresponding screw thread 151 on lens assembly 150 so that housing 110 and lens assembly are rendered as a single unit (i.e., light assembly 100).

Although a screw thread is illustrated, it would be recognized that housing 110 and lens assembly 150 may be joined by other means. For example, housing 110 and lens assembly 150 may be joined together using a bayonet connection, a snap-fit connection, a form fit connection and other similar connections, without altering the scope of the invention.

Further shown, on lens assembly 150, are grooves 154 that substantially circumvent lens assembly 150. Grooves 154, which is an optional feature of lens assembly 150, provide for an increased surface area to distribute heat generated within lighting element 100, as will be explained.

Figure 2:
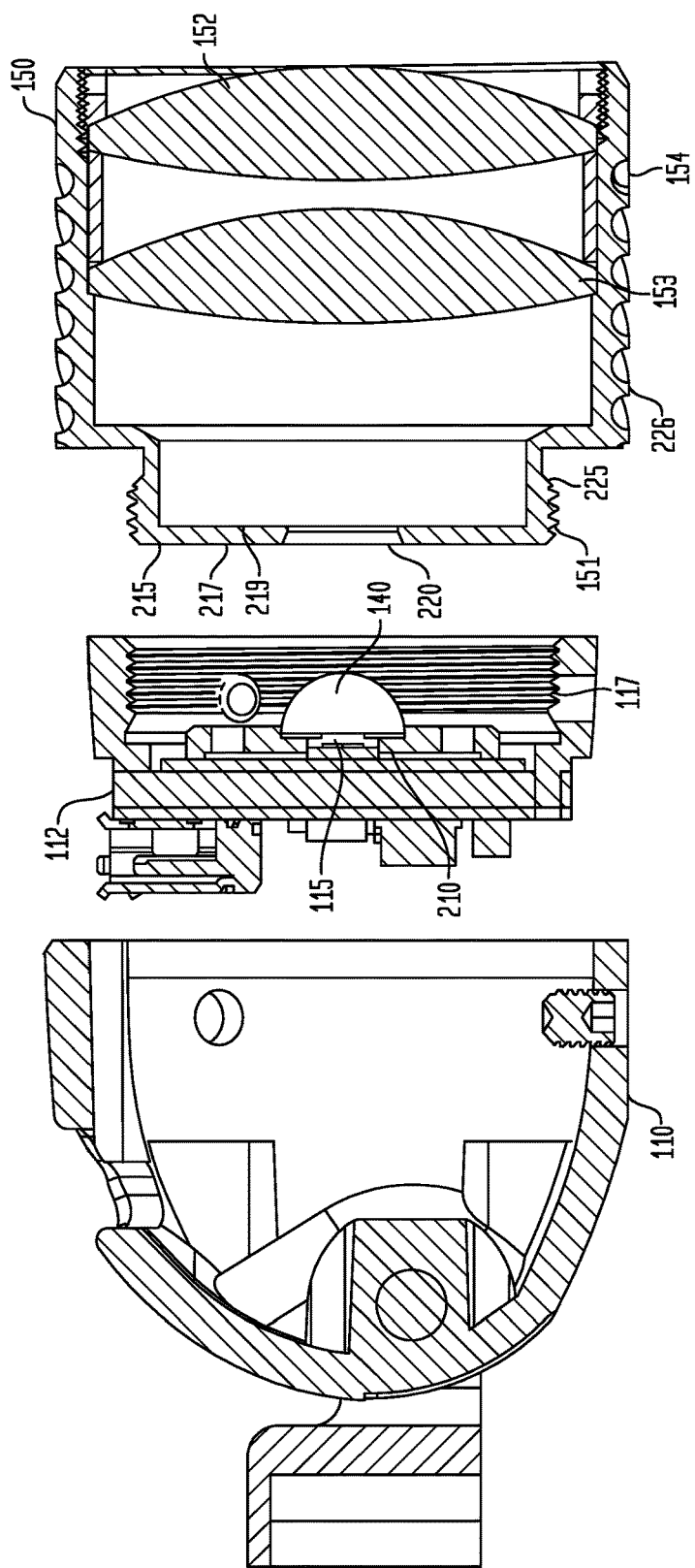
FIG. 2 illustrates a cross-sectional view of a light assembly in accordance with the principles of the invention.

FIG. 2 illustrates a cross-sectional view of the exemplary light assembly 100 shown in FIG. 1 in accordance with the principles of the invention.

In this exemplary embodiment, the lens assembly 150, which is substantially cylindrical comprises a first section 226 (i.e., a lens section) and a concentrically mated second section 225 (i.e., an attachment section) integrally incorporated onto first section 226. First section 226 houses at least one lens (of which two are shown 152, 153). Second section 225 includes threads 151, formed on and circumscribing the outer surface of attachment section 225. Thread 151 provides, in this illustrative example, a means for attaching the lens assembly 150 to the housing 110.

In the exemplary embodiment shown, lens assembly 150 is mated to housing 110 by engaging screw thread 151 on attachment section 225 with internal screw thread 117 of housing 110, wherein screw thread 151 and screw thread 117 are of a matching thread characteristic (i.e., thread count/inch, pitch).

Although screw thread 151 is shown as an external thread and screw thread 117 as an internal thread, it would be recognized that the screw thread 151 may be an internal screw thread while screw thread 117 may be an external screw thread, without altering the scope of the invention.

Similarly, the use of a bayonet connection, a snap-fit connection or a form-fit connection may be utilized to attach lens assembly 150 to housing 110 without altering the scope of the invention. Bayonet, snap-fit and form-fit connections are well-known in the art and those with knowledge in the art would recognize and understand other means for adapting the exemplary threaded connection, discussed herein, with another type of connection, based on a reading of the teachings provided herein.

For example, regarding a bayonet connection, it would be understood that the attachment section 225 may comprise a plurality of nipples or tabs extending from an outer surface of attachment section 225. The nipples may engage a plurality of "L-shaped" grooves or depressions within the housing 110, wherein after a nipple engages a corresponding first leg of the "L-shaped" groove, a twist of lens assembly 150 forces the nipple to engage a second leg of the corresponding "L-shaped" groove. Thus, the lens assembly is "locked" in place with (i.e., attached to) housing 110.

While both a thread attachment and a "bayonet" attachment are disclosed, it would be recognized by those skilled in the art that other types of attachment mechanisms may be incorporated into the subject matter disclosed; such other type of attachment mechanisms have been contemplated and considered to be within the scope of the invention claimed.

Further shown in FIG. 2 is at least one biconvex lens 152 within lens assembly 150. In the exemplary embodiment illustrated, two lenses 152 and 153 are shown. The at least one biconvex lens(es) 152 (153) provide a means for focusing light provided by LED 115 onto a surface at a known distance from the at least one lens 152 (153). It would be understood by those skilled in the art that the number of lens may be increased or decreased without altering the scope of the invention.

Although a biconvex lens is shown it would be recognized that the lens may be one or more of a plano convex lens, a meniscus lens (which is convex and slightly concave) or an aspheric lens without altering the scope of the invention claimed. The lens(es) 152 (153) may be composed of glass or plastic without altering the scope of the invention claimed.

Further illustrated is lighting element 112 comprising printed circuit board (PCB) 210, LED 115, electrically connected to, and positioned on PCB 210. LED 115 is positioned on PCB 210 along an optical axis substantially centered with the biconvex lens(es) 152 (153), when lens assembly 150 is joined to housing 110. PCB 210 provides for control of a current, provided by a voltage or power source (not shown), that may be applied to LED 115. The voltage applied to LED 115, through PCB 210, may, for example, be provided by a battery (DC voltage) or a low-voltage alternating current (AC) that is subsequently rectified to provide a rectified DC voltage at the input of LED 115. The source(s) of voltage (i.e., the battery or the rectified AC/DC voltage) are not shown. However, such sources are well-known in the art and their structure(s) and/or operation are known to those skilled in the art and need not be discussed herein.

PCB 210 may further include a switch (not shown) that may be used to control a flow of electrical energy (i.e., voltage/current) to LED 115. For example, in a first position, the switch may prevent a voltage from being applied to LED 115; whereas in a second position, the switch may be set to allow a voltage to be applied to the LED 115. The switch may be an electronic switch (e.g., diode, transistor) or a mechanical switch. Control of the switch may be performed in response to a mechanical input or an electronic input.

In another aspect of the invention, PCB 210 may include a current regulator circuit (not shown), wherein voltage applied to LED 115 is substantially constant (i.e., 3.7 volts) and the current to LED 115 is varied. The current regulator circuit may include components that are designed to limit or vary (i.e., increase or decrease) the current applied to LED 115. In one aspect of the invention, the current regulator circuit may set the current to one of a plurality of fixed values, such that the intensity of light outputted by LED 115 is changed based on which of the plurality of fixed values is applied to LED 115. In another aspect of the invention, the current regulator circuit may increase (or decrease) the current applied to LED 115 over a fixed period of time. In another aspect of the invention, the current regulator circuit may provide a switched current to LED 115. That is, the current may be alternatively applied to and removed from LED 115. The alternating application/removal of the current to/from LED 115 causes LED 115 to be turned on/turned off, which due to the persistence of the human eye is not noticed by the user. In this case, the ability of the current regulator circuit to limit the duration of current to LED 115 may increase the duration of the voltage source (e.g., a battery) as LED 115 is not continuously drawing energy from the source. As would be understood, the PCB 210 may further include a voltage regulator circuit that provides a substantially constant and/or consistent voltage to LED 115.

Further illustrated is dome lens 140 substantially proximate to and centered with respect to LED 115. Dome lens 140 provides for a magnification of the light outputted by LED 115. The degree of magnification provided by dome lens 140 is based at least on the curvature of dome lens 140 and the index of refraction of the material selected for dome lens 140.

Figure 8:
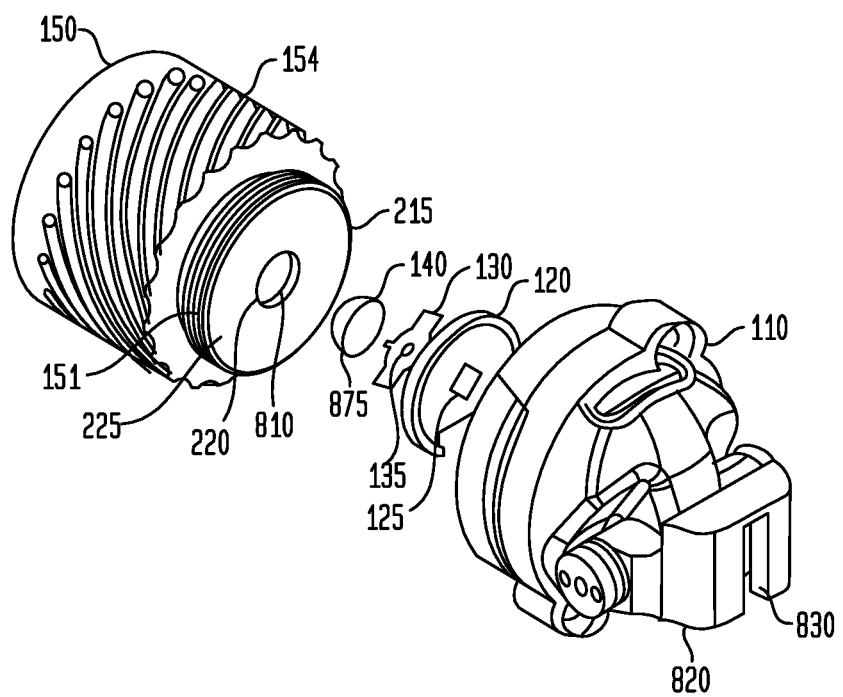
FIG. 8 illustrates an exploded perspective rear view of the light assembly shown in FIG. 1.

Further shown, on lens assembly 150 is rear surface 215 (i.e., a closed surface) of attachment section 225 (see FIG. 8). Rear surface 215, which is representative of a retention means, includes a retainer (i.e., an opening (or passthrough) 220 (see FIG. 2). Opening 220, which passes from a first (outer) surface 217 of retainer 215 to a second (inner) surface 219 of retainer, is substantially centered within retainer 215, and provides a means of centering and retaining dome lens 140 onto (or in close proximity to) LED 115, without the use of an adhesive or similar materials.

In accordance with the principles of the invention, without the use of any glue or adhesive to retain dome lens 140 onto LED 115, the problems of out-gassing and fogging are removed. That is, as is known in the art, the use a glue or adhesive and a retaining ring to retain a lens onto an LED is problematic as the heat generated by the LED and electronic component on PCB 210 heats the glue or adhesive. The heated glue or adhesive then generates gases that fog the surface of the lens. In the illustrated embodiment shown in FIG. 2, outgassing caused by a heated glue or adhesive will not fog the inner facing surface of lens 153.

In accordance with the principles of the invention, opening 220 within rear surface (retention means) 215 is formed such that the edges (surfaces) of opening 220 substantially match, or conform to, a radius of curvature of lens 140. As lens assembly 150 is attached to housing 110 (e.g., threads 117 engaging threads 151), dome lens 140 is substantially self-centered within opening 220 and on (or in close proximity to) LED 115, without any use of adhesive or glue.

Although the edges (surface) of opening 220, within retention means 215, are shaped to engage or contact a radius of the lens 140, it would be recognized that the edges of opening 220 may be machined to tangentially (i.e., a straight line) engage or contact the radius of curvature of the lens 140. Alternatively, the edges of opening 220 may be machined to partially conform to the shape of dome lens 140.

In a fully or partially conformal fitting the surface (edges) of opening 220 substantially match a radius of curvature of lens 140. A conformal shaping of the surface of opening 220 is determined based on the characteristics of dome lens 140. As would be recognized, the conformal shape of surface of opening 220 may fully match the radius of curvature of lens 140 or may match only a portion of the lens 140. In one aspect of the invention, a thickness of retainer 215 may determine an amount of contact of a conformally shaped surface of opening 220 as a thicker surface or retainer 215 allows for a more conformal shaping of the surface or edges of opening 220.

In accordance with another aspect of the invention, in a tangential fitting (i.e., the edges (surface) of opening 220) may be chamfered, such that the surfaces of opening 220 are determined by the degree of chamfer desired. As would be recognized, a thickness of 215 may determine a chamfer angle, which allows for the edges or surface of opening 220 to sufficiently contact dome lens 140.

In one aspect of the invention, the attachment section 225 (including threads 151) may be constructed of a heat transferable medium to draw heat generated by the electronic components on PCB 210 away. For example, attachment section 225 may be constructed from at least one of a copper, a tellurium, a copper tellurium alloy, an aluminum, or other similar type of heat conductive materials and alloys. Similarly, lens section 226 may be constructed of a similar heat transferable medium (e.g., aluminum, copper, tellurium, copper tellurium alloy, etc.). In one embodiment, aluminum may be selected as a suitable material for lens assembly 150 (i.e., lens section 226, attachment section 225) as aluminum is light weight and a good heat conductor. However, other suitable heat transfer mediums may be utilized without altering the scope of the invention (e.g., copper, tellurium, copper tellurium alloy, etc.). In accordance with the principles of the invention, attachment section 225 (including retention means 215) and lens section 226 may be constructed from a single heat conductive material such that attachment section 225 (including retainer 215) and lens assembly 225 are an integral piece. Alternatively, retention means 215, attachment section 225 and lens section 226 may be constructed of different materials and then joined together, permanently, to each other. Alternatively, retention means 215, attachment section 225 and lens section 226 may be of a same or of different heat transferable materials which may be removable joined together.

In accordance with the principles of the invention, heat generated by LED 115/electronic components on PCB 210 may be transferred, through the engagement of the attachment section 225 (i.e., a coupler) to lens section 226, wherein the heat generated by PCB 210/LED 115 may be dispersed into the surrounding environment.

As is further shown, lens section 226 of lens assembly 150 includes a plurality of grooves (i.e., deformations) 154 (or a single groove diagonally circumscribing housing 150), that extend circumferentially around lens section 226. The incorporation of groove(s) 154 into lens section 226 (i.e., lens assembly 150) is advantageous as it provides for an increased surface area, from which heat may be dispersed.

Although, FIG. 2 illustrates a plurality of grooves 154 within lens assembly 150 (or a single groove circumferentially around lens assembly 150), it would be recognized that lens assembly 150 may include a plurality of protrusions, extensions, bumps or ridges (or a single protrusion diagonally circumscribing lens assembly 150) (not shown) that extend from an outer surface of lens assembly 150. The (not shown) protrusions on lens assembly 150 also increase the surface area of lens assembly 150 to increase the efficiency of dispersing the generated heat into the surrounding environment. In addition, grooves 154 (or protrusions) may be spirally positioned (i.e., one continuous groove or protrusion on the outer surface), concentrically positioned (i.e., a plurality of circular grooves or protrusions) and/or longitudinally positioned (a plurality of grooves or protrusions longitudinally positioned on the outer surface), without altering the scope of the invention. As would be recognized grooves (or protrusions) 154 may represent deformations within (or on) an outer surface of lens assembly 150.

In another aspect of the invention, PCB 210 may be in contact with attachment section 225, such that the heat generated by the LED 115 and the electronic components on PCB 210 may be transferred to lens assembly 150. For example, a heat conductive material (e.g., copper wire or copper ring) may contain PCB 210, therein, wherein the copper wire or copper ring contacts the attachment section 225 so as to transfer the heat of LED 115/PCB 210 through the copper ring element 305 to lens assembly 150.

In accordance with the principles of the invention, the operation of light assembly 100 remains consistent as the heat generated by the LED 115 is efficiently removed from the interior of the light assembly 100.

Figure 3A:
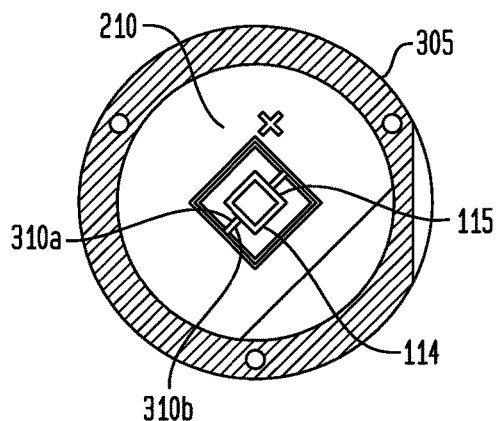
FIG. 3A illustrates an exemplary front view of a circuit board contained within the housing shown in FIG. 1.

FIG. 3A illustrates a front view an exemplary embodiment of a ring element 305 showing PCB 210 contained therein. Further illustrated is LED 115 substantially centered on PCB 210. Electrical connections 310a and 310b provide electrical energy (voltage/current) to LED 115. Further illustrated is border 114 surrounding LED 115. Border 114 represents an area in which the LED 115 outputs a light that is not substantially white.

That is, white LEDs are manufactured using a combination of a blue LED and a yellow phosphor. White light is perceived when blue light from the LED is mixed with a yellow light that is emitted from the phosphor. In the illustrated embodiment shown, the blue LED portion of LED 115 is substantially centered in LED 115, and is in contact with a phosphorus layer (represented as border 114). The mixture of the blue LED light with the yellow light of the phosphorus layer causes a white light to be visible.

Figure 3B:
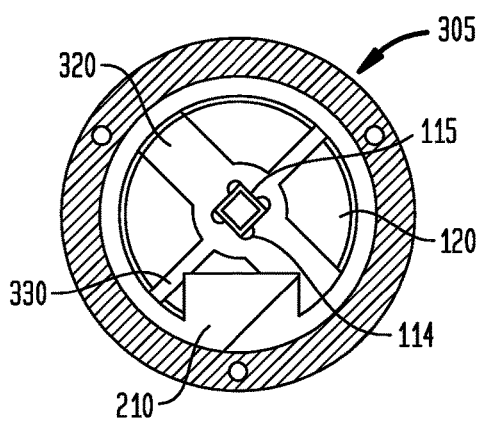
FIG. 3B illustrates a second aspect of the exemplary front view of a circuit board shown in FIG. 3A.

FIG. 3B illustrates a second aspect of the exemplary front view shown in FIG. 3A, wherein aperture holder 120 is positioned on PCB 210. Aperture holder or plate 120 includes a first groove (i.e., depression) 320 extending a length (e.g., diameter) of aperture holder 120. Further shown is second groove (i.e., depression) 330 extending substantially the length of aperture holder and oriented substantially perpendicular to first groove 320.

Returning to FIG. 1, FIG. 1 further illustrates the incorporation of first groove 320 and second groove 330 within aperture holder 120. Further shown is opening 125 of aperture holder 120 at the intersection of the first groove 320 and second groove 330. Opening 125 is centered within aperture holder 120 and sized to enable at least the blue LED portion of LED 115 to be viewed therethrough.

Figure 3C:
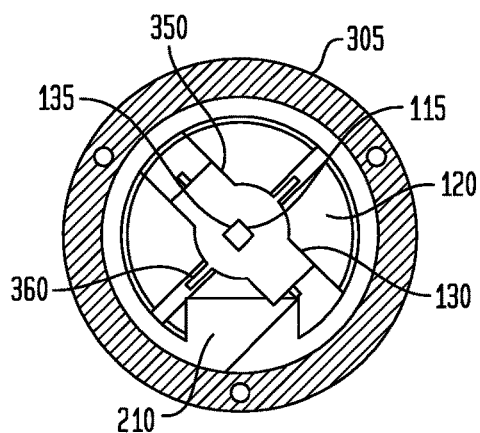
FIG. 3C illustrates a third aspect of the exemplary front view of a circuit board shown in FIG. 3B.

FIG. 3C illustrates a third aspect of the exemplary front view shown in FIGS. 3A, 3B, wherein aperture 130 includes a first leg 350 and a second leg 360 substantially perpendicular to first leg 350. An opening 135 in aperture 130 is positioned at an intersection of the first leg 350 and the second leg 360. As shown, first leg 350 is positioned within first groove 320 and second leg 360 is positioned within second groove 330 of aperture holder 120. Further illustrated is opening 135 centered over LED 115. Opening 135 is sized such that only a center section (i.e., blue LED portion) of LED 115 is viewable through opening 135. Aperture holder 120 and aperture 130 limit stray light generated by the phosphorous layer (i.e., border 114) from being viewable.

First groove 320 and second groove 330 of aperture holder or plate 120 allow for the proper positioning and alignment of aperture 130 onto or in close proximity to LED 115. Although grooves 320 and 330 on aperture holder 120 are illustrated and discussed, in an alternative embodiment grooves 320 and 330 may be holes within aperture holder 120 into which tabs of aperture 130 may be inserted in order to align aperture 130 with aperture holder 120.

Figure 3D:
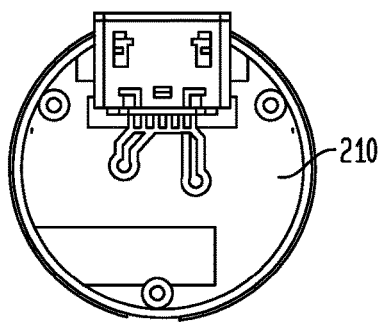
FIG. 3D illustrates an exemplary rear view of a circuit board shown in FIG. 3D.

FIG. 3D illustrates a back view of PCB 210 showing the substrate forming PCB 210 and exemplary components and electrical connections used in controlling the application (or the removal) of a voltage and current to LED 115. Electrical components on PCB 210 may comprise one or more passive devices, such as resistors, capacitors and inductors and one or more active devices, such as transistors and diodes. These components may be joined together to form a controller that is usable in controlling the operation of the LED 115. In another aspect of the invention, the components may include a microprocessor, a microcontroller or a special purpose integrated circuit (e.g., Application Specific Integrated Circuit) that includes processing to control the application, or removal, of a voltage/current from LED 115.

In addition, components suitable for operation with the transmission and reception of signals for controlling the application of voltage/current to LED 115 may be incorporated on PCB 210. For example, components associated with an IR (infra-red) transmitter and receiver may be incorporated onto PCB 210. IR components may, for example, be used to transmit an IR signal, which when a reflection of such signal is detected by the IR receiver, cause the generation of a signal that may be provided to the controller to control the application of a voltage/current to LED 115 (i.e., turn on and/or turn off). Similarly, the signal provided to the controller associated with the detected IR signal may be used to alter (increase/decrease) the voltage/current applied to LED 115. Although IR signal is discussed it would be recognized that the transmitter and receiver may be associated with RF (radio frequency) and/or audio (ultra-sonic waves). U.S. Pat. No. 8,215,791, which is assigned to the Assignee of the instant application, the contents of which are incorporated by reference, herein, discloses operation of such IR signal control.

In another aspect of the invention, PCB 210 may include components that are associated with voice recognition, wherein a verbal command such as "turn-on", "turn-off", "Raise, "Lower," may provide signals to the controller such that a corresponding alteration of the voltage/current to LED 115 may be effected.

Figure 4A:
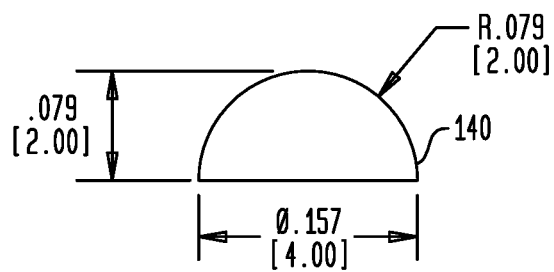
FIG. 4A illustrates an exemplary dome lens in accordance with the principles of the invention.

FIG. 4A illustrates a cross-sectional view of an exemplary dome lens 140 in accordance with the principles of the invention. In this illustrate example, the dome lens 140 is represented as being of substantially of a semi-spherical shape. Dome lens 140 may be constructed or fabricated, for example, by removing a portion of a spherical, substantially clear material, along a diameter of the sphere. As would be known in the art, the sphere diameter divides the sphere into two equal halves; a hemispherical shape, which in a cross-sectional view is represented by a semi-circular shape. In a more general sense, dome lens 140 may be constructed or fabricated by removing a portion of the spherical material along a chord of the spherical material.

As would be known in the art, the shape of dome lens 140 and the index of refraction of the material from which the sphere is created determines a degree of magnification of dome lens 140. In this illustrated cross-sectional view of dome lens 140, dome lens 140 is of a semi-circular shape having a radius of 2 mm (millimeters) as the original spherical shape has a diameter of 4 mm.

Figure 4B:
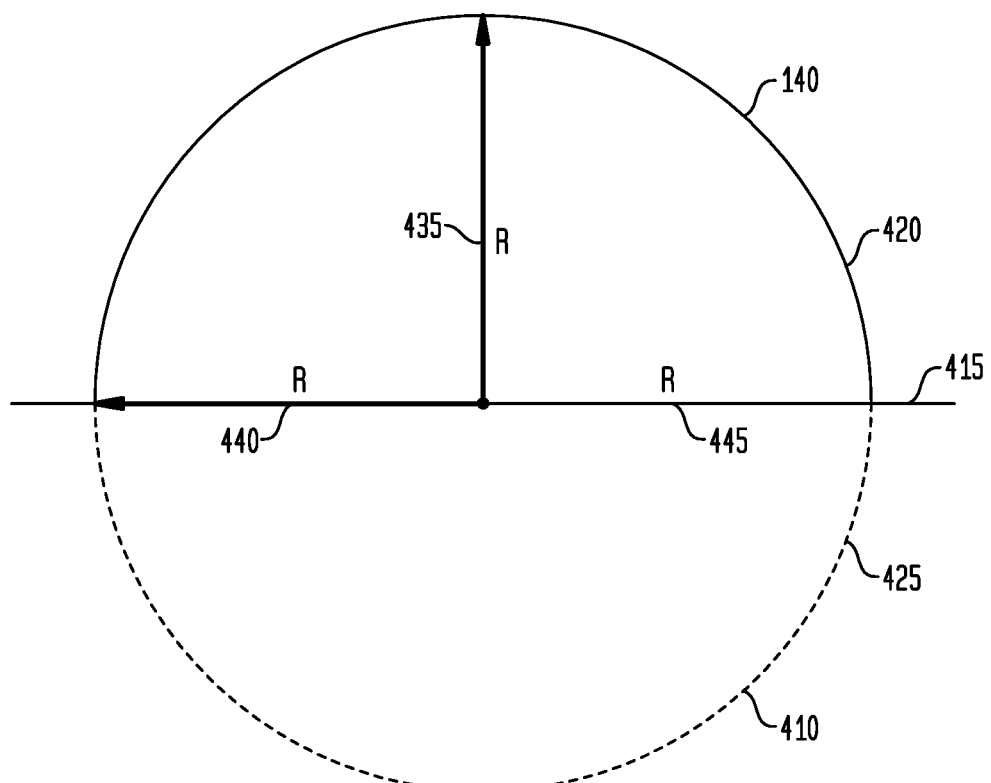
FIG. 4B illustrates exemplary characteristics of the dome lens shown in FIG. 4A.

FIG. 4B illustrates exemplary characteristics of the spherical shape 410 used to form dome lens 140 shown in FIG. 4A. In this illustrated embodiment, dome lens 140 is constructed or manufactured by dividing or dissecting sphere along its diameter 415. By dividing sphere 410 along its diameter, two equal (i.e., hemispheric or semi-spherical) elements 420, 425 are formed. In this illustrated embodiment, dome lens 140 is represented by one of the two hemispheric elements.

In this exemplary dome lens 140 construction, measures 435, 440, 445, extending from a central point of the spherical material are equal in both the horizontal and in the vertical (i.e., perpendicular to the horizontal) direction.

Figure 4C:
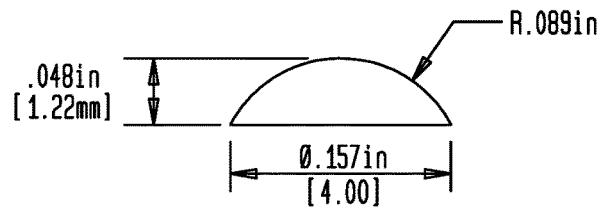
FIG. 4C illustrates a second exemplary dome lens in accordance with the principles of the invention.

FIG. 4C illustrates a cross-sectional view of a second exemplary dome lens 140 having a 4 mm diameter which is constructed or fabricated by removing or dividing the spherical element along a chord different than the diameter. In this illustrated example of a 4 mm sphere, the measure extending substantially perpendicular to the horizontal axis is smaller than those measures along the horizontal axis.

Figure 4D:
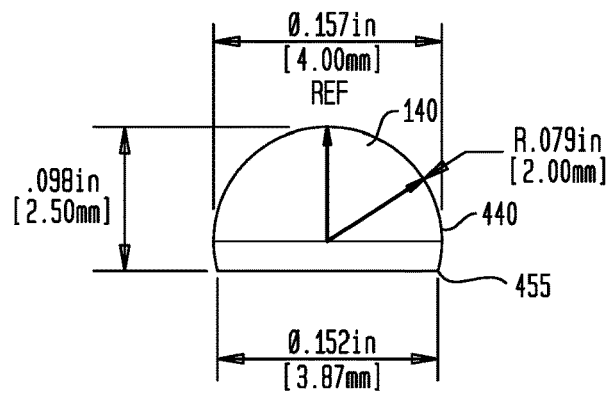
FIG. 4D illustrates a third exemplary dome lens in accordance with the principles of the invention.

FIG. 4D illustrates a cross-section of a third exemplary dome lens 140 in accordance with the principles of the invention.

In accordance with the principles of the invention, an exemplary dome lens 140 may be constructing from a 4 mm sphere (i.e., radius 2 mm), by trimming (cutting, shaving) along choral axis 440, such that a length of the dome lens 140, which is measured from the choral axis 440 to an edge of the dome lens 140 is greater than the radius (i.e., 2 mm) of sphere.

Figure 4E:
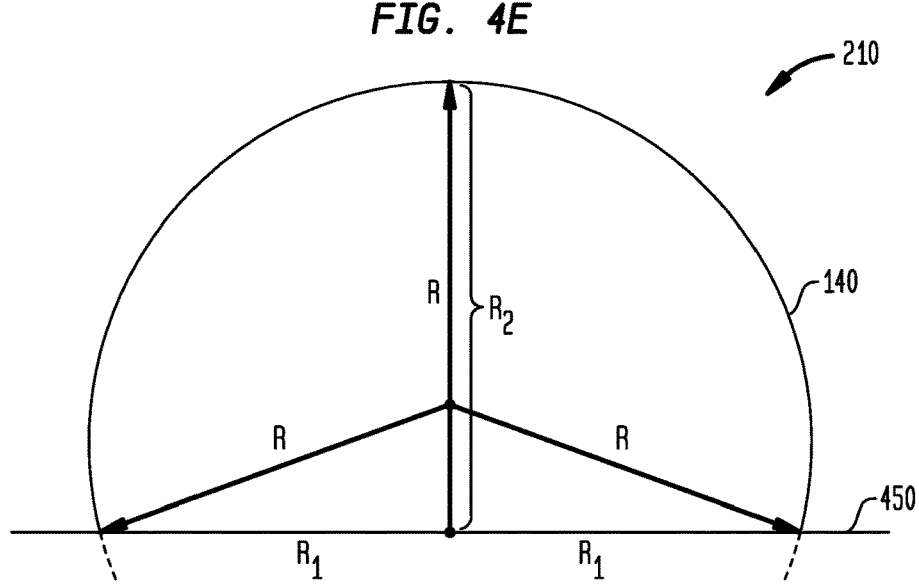
FIG. 4E illustrates exemplary characteristics of the dome lens shown in FIG. 4D.

FIG. 4E illustrates an exemplary characteristics of dome lens 140 shown in FIG. 4D.

In this exemplary embodiment, a spherical element is machined along chord 450 such that dome lens 140 possesses an equal length element along the chordal (horizontal) direction (R1), while the length (R2), in the substantially perpendicular direction, is greater than that of R1.

As would been known to those skilled in the field of mathematics, a spherical cap, a spherical dome or a spherical segment may be determined or formed from a portion of sphere cut off by a chordal plane. When the chordal plane passes though the center of the sphere, so that the height of the cap is equal to the radius of the sphere, the spherical cap is referred to as a hemisphere. However, the cap (i.e., dome lens 140) may be of another shape, as shown in FIGS. 4C and 4D, by passing a chordal plane through a different section of the sphere that is not the diameter of the sphere.

In accordance with the principles of the invention, the increased length of the dome lens 140 in a substantially perpendicular direction (i.e., vertical) from the chordal plane increases the magnification capability of the lens element. The increased magnification provides for a greater projection of light.

Using well known geometric principles, the cord lengths (R1, R2) shown in FIG. 4E, for example, may be determined from conventional mathematical formulas and need not be discussed herein.

FIGS. 4A-4E illustrate exemplary dome lens 140 configurations suitable for use in lighting element 112 discussed herein. However, it would be recognized by those of ordinary skill in the art, that various modifications and changes to the construction of a dome lens 140 can be made without departing from the scope of the invention as set forth in the claims. Such modifications and changes have been contemplated and are considered to be within the scope of the invention claimed. For example, while it is disclosed that dome lens 140 may be fabricated from a spherical element, if would be recognized that dome lens 140 may be fabricated as a desired shape by successive depositing of layers of optically clear materials onto an optically clear substrate, without altering the scope of the invention.

Figure 5A:
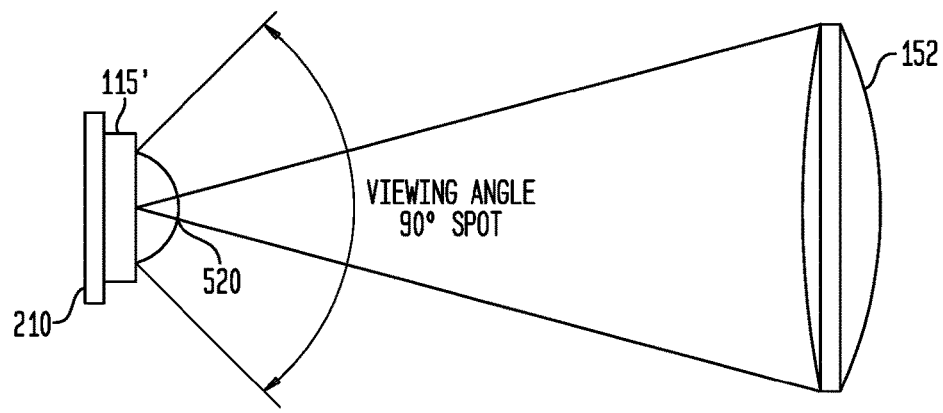
FIG. 5A illustrates a side view of an exemplary conventional lighting configuration.

FIG. 5A illustrates an exemplary conventional LED lighting element configuration. In this exemplary configuration, LED 115' (which represents a typical conventional (older technology) LED), is positioned on PCB 210 and is positioned behind lens 152 such that LED 115' is positioned at a focal point 510 of lens 152. LED 115' is covered by a lens, which, as has been discussed, is held in place using a glue or adhesive.

The conventional LED 115' illustrated is of a size of 3 mm×3 mm (i.e., 9 square mm), which provides a desired illumination output for a known current input.

Figure 5B:
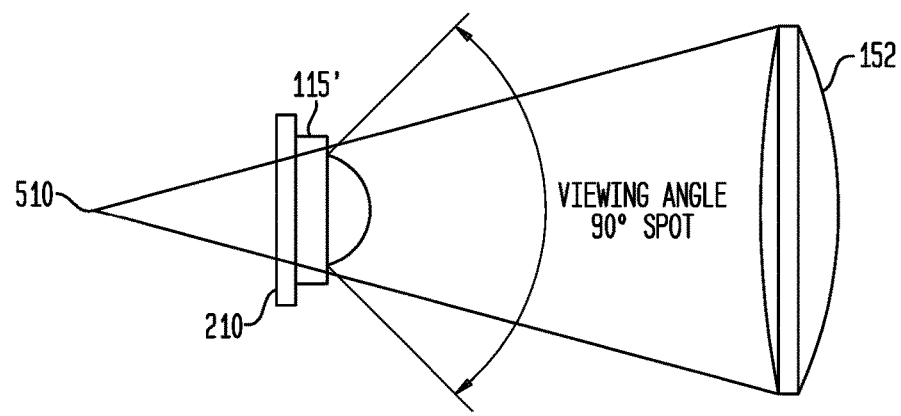
FIG. 5B illustrates a side view of a second exemplary conventional lighting configuration.

FIG. 5B illustrates a second exemplary LED configuration, similar to that disclosed in U.S. Pat. Nos. 7,690,806 and 8,215,791, which are assigned to the Assignee of the instant application, and whose contents are incorporated by reference, herein.

In this second exemplary configuration, a conventional LED 115' is positioned behind lens 152 such that LED 115' is positioned within the focal point 510 of lens 152. In this second exemplary configuration, the light generated by LED 115' is focused (i.e., de-focused) to improve the presentation of the light projected onto a surface (not shown).

FIG. 6 illustrates an exemplary light element configuration similar to that shown in FIG. 5B using contemporary (i.e., current technology) LED 115. As the LED 115 is smaller (i.e., 1 mm×1 mm) than a typical conventional LED 115' (FIG. 5A), the amount of light that passes through lens 152 is less due to the decreased LED die size.

FIG. 7 illustrates an exemplary lighting element configuration in accordance with the principles of the invention.

As shown, LED 115 is positioned on or in close proximity to dome lens 140 and is further positioned within a focal length 510 of lens 152 and within a focal length 720 of dome lens 140. Although FIG. 7 illustrates LED 115 being positioned within the focal length 720 of dome lens 140, it would be appreciated that LED 115 may be positioned at the focal element 720 of dome lens 140, without altering the scope of the invention.

In this illustrated embodiment of the invention, the light generated by LED 115 is first focused (or de-focused) by dome lens 140 to produce a light having a smaller (i.e., narrower angle) distribution such that a greater amount of light from LED 115 is directed toward lens 152. The light directed toward lens 152 is then projected on to a surface (not shown) at a known distance from lens 152 to provide a brighter and substantially uniform light distribution pattern on the surface.

In an alternative embodiment, and similar to that shown in FIG. 1, an aperture holder 120 and aperture 130, which is, held in place by aperture holder 120 are included. Aperture 130 includes an opening 135, through which the light generated by LED 115, passes. The use of aperture 130 is advantageous as it limits the light generated by the phosphorous portion (i.e., border 114) of LED 115. Aperture 130, thus, defines that light projected onto a surface at a known distance from lens 152.

FIG. 8 illustrates an exploded rear perspective view of the light assembly 100 in accordance with one embodiment of the invention.

In this illustrated aspect of the invention, which is similar to that shown in FIG. 1, threads 151 are formed on the outer surface of attachment section 225. As previously discussed, housing 110 engages lens assembly 150 by engaging threads 151 to thread 117 (not shown) in housing 110. Further illustrated are aperture holder 120, aperture 130 and dome lens 140, as previously discussed. Also illustrated is opening 220 formed within retention means 215 of the attachment section 225. Surface 810, formed by the opening 220 provides a means for retaining and centering dome lens 140.

To provide for a self-centering of dome lens 140 within opening 220, surface 810 is formed to be substantially comparable (e.g., conformal) to the shape of dome lens 140.

In accordance with one aspect of the invention, the surface (i.e., ridge, edge) 810 may be formed to match the curvature curved shape of dome lens 140. In accordance with another aspect of the invention, surface (i.e., ridge) 810 may be chamfered (i.e., angled) such that the ridge 810 tangentially contacts lens 140.

Figure 9A:
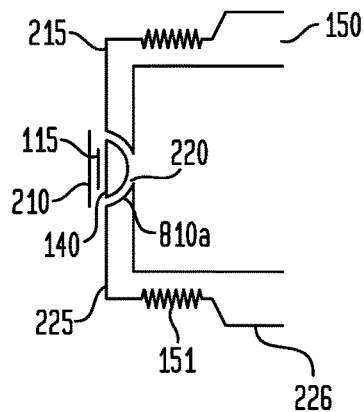
FIGS. 9A-9C illustrate cross-sectional views of exemplary embodiments of the invention showing the retaining of a dome lens in accordance with the principles of the invention.
Figure 9B:
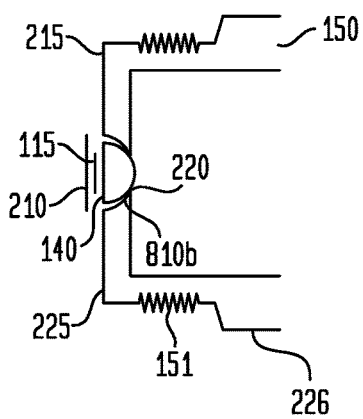
Figure 9C:
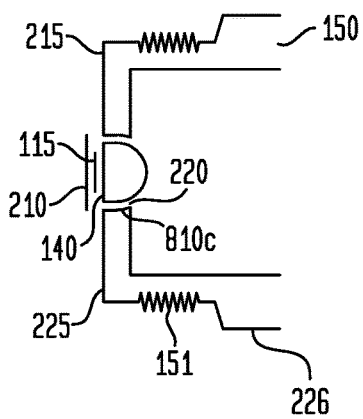

FIG. 9A, FIG. 9B and FIG. 9C illustrate exemplary configurations of surface 810 in accordance with the principles of the invention.

FIG. 9A illustrates a cross-sectional view of an exemplary engagement of surface 810 (labelled 810a) formed to match a radius of curvature (conformal fit) of dome lens 140.

FIG. 9B illustrates a cross-sectional view of an exemplary engagement of surface 810 (labelled 810b) to dome lens 140, wherein surface 810 is chamfered, at a first angle, to tangentially contact lens 140.

FIG. 9C illustrates a cross-sectional view of a second exemplary engagement of surface 810 (labelled 810c) to dome lens 140, wherein surface 810 is chamfered, at a second angle, to tangentially contact domed lens 140. As would be appreciated, the angle of the chamfer and the radius of curvature of the dome lens 140 determines an amount of contact surface 810 has with domed lens 140.

As would be recognized, the angle of chamfer of surface 810 determines a point (or points) of contact of surface 810 with dome lens 140. As would be further recognized, the angle of chamfer determines a size of opening 220 through which dome lens 140 protrudes. As would be further recognized, the angle of chamfer (or the radius of curvature) depends on a size of the dome lens 140 (i.e., the radius of curvature). Hence, the angle of chamfer or the radius of curvature of surface 810 may be altered and adapted to comport with the radius of curvature of the selected domed lens 140.

Returning to FIG. 8, further illustrated is an anti-reflective coating 875 on a surface (i.e., rear and/or dome) of dome lens 140. Anti-reflective coating 875 is advantageous as it reduces reflections of the light generated by LED 115 from the back surface of dome lens 140.

Figure 10A:
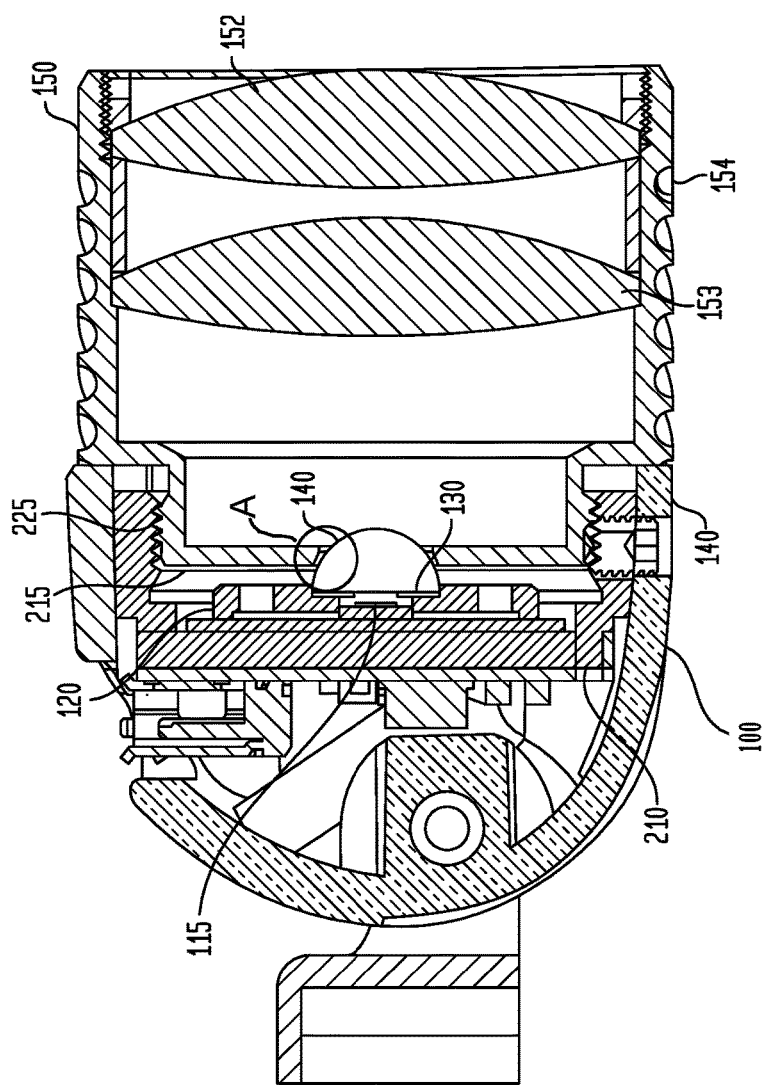
FIG. 10A illustrates a cross-sectional view of an exemplary lighting element in accordance with the principles of the invention.

FIG. 10A illustrates a cross-sectional view of light assembly 100, similar to that shown and described with regard to FIG. 2. In this illustrated view, an enlargement (i.e., a circled area, labelled "A"), illustrates the retention of dome lens 140 by surface 810 in opening 220 of retention means 215.

Figure 10B:
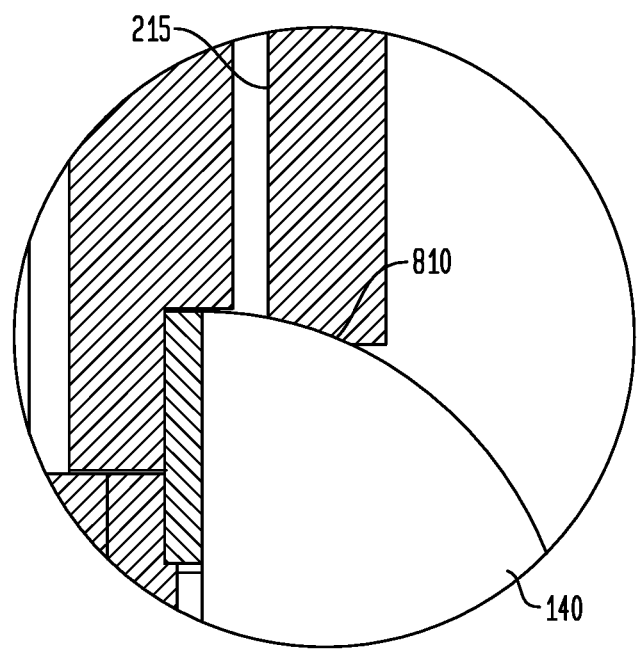
FIG. 10B illustrates an expanded view of the area indicated as A in FIG. 10A, in accordance with a first aspect of the invention.

FIG. 10B illustrates an expanded view of the area labelled "A" in FIG. 10A showing the fit, connection or contact between the dome lens 140 and surface 810. In this illustrated exemplary embodiment, the surface 810, which contacts dome lens 140, is represented as a substantially conformal fit, wherein surface 810 follows all or a portion of the curvature of lens 140.

Figure 10C:
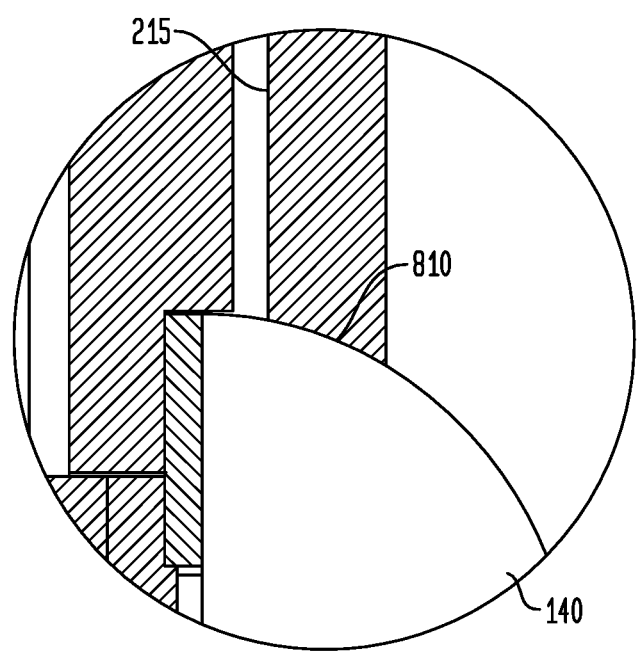
FIG. 10C illustrates an expanded view of the area indicated as A in FIG. 10A, in accordance with a second aspect of the invention.

FIG. 10C illustrated an expanded view of the area labelled "A" in FIG. 10A, wherein the surface 810 is configured to fully conform to the curvature of lens 140.

As would be recognized, the degree of conformity of surface 810 to the curvature of lens 140 is determined based on the degree to which such conformity is desired, the ability of manufacturing machines to machine or form surface 810 and a thickness of rear surface 215.

FIG. 11A illustrates an exploded perspective view of PCB 210 and a housing attachment section 1130, in accordance with the principles of the invention. In this illustrated embodiment, PCB 210 is contained within a ring or holder 1110, which is composed of a heat transferable material (e.g., copper, aluminum, etc.). Ring or holder 1110 is comparable to holder 305 shown in FIG. 3A.

As discussed, the heat generated by components positioned on PCB 210/LED 115 may be transferred through the ring or holder 1110 to the lens assembly 150 to draw heat generated by the LED/PCB components away from the electronic components.

Although the term "ring" is used to describe element 1110, it would be recognized that element 1110 may be constructed as a plate of a heat transferable material into which a depression or cavity is formed. PCB 210 may then be placed and retained within the depression or cavity of the plate. Or PCB 210 may simply be placed on a plate of heat transferable material.

In the exemplary embodiment shown, on surface of ring 1110 are a plurality of alignment holes or depressions 1120 that project into a surface of ring 1110. Further shown is housing attachment section 1130, including a plurality of pegs 1135, extending substantially perpendicular to the attachment section 1130 and an internal screw thread. Internal screw thread, may, in one aspect of the invention correspond to internal screw thread 117, shown in FIG. 1.

In this illustrated embodiment, when housing attachment section 1130 is joined with ring 1110 (see FIG. 11B), pegs 1135 are inserted into corresponding holes (depressions) 1120. Both ring 1110 and housing attachment section 1130 are constructed from a heat conductive medium, such that the heat of PCB 210/LED 115, caused by the operation of the electronic components thereon, is transferred to the housing section 1130. As previously discussed, this generated heat is subsequently transferred to the lens assembly 150 (not shown) by the attachment of housing 110 to lens assembly 150. Hence, the joined ring 1110 and housing attachment 1130 operate as a heatsink to remove heat generated by LED 115/electronic components on PCB 210. Attachment section 1130 may then be solder connected to ring 1110 to provide for better heat transfer between the two elements.

Although ring 1110 and section 1130 are shown attached using alignment pegs, it would be recognized that the ring 1110 and attachment section 1130 may be attached through a screw thread attachment, a bayonet fit attachment, a snap fit attachment, a form fit attachment, a butt fit attachment, etc., without altering the scope of the invention. Screw thread, bayonet, snap-fit and butt fit attachment means have been previously discussed and need not be discussed further herein.

FIG. 11C illustrates another aspect of the housing 110, shown in FIG. 1, wherein the ring element 1110 and attachment 1130 are contained therein.

Further shown is lighting element 112 including PCB 210, and LED 115. Aperture holder 120 and aperture 130 are further illustrated.

In this illustrated case, ring 1110 and attachment section 1130 are sized to contact housing 110. Screw thread 117 is contained within the attachment section 1130 and operates in a manner similar to that discussed with regard to FIGS. 1 and 2.

As previously discussed, PCB 210 within ring 1110 (see FIG. 3A, FIG. 11A) provides for the transfer of heat generated by the component on PCB 210 and/or LED 115 away from PCB 210 and LED 115. In this illustrated case, the heat is transferred to housing 110.

It would be appreciated that attachment means 225, when connected to housing 110, through screw thread 117, provides further surface area to which heat may be transferred away from PCB 210 and LED 115 through lens assembly 150.

Figure 12A:
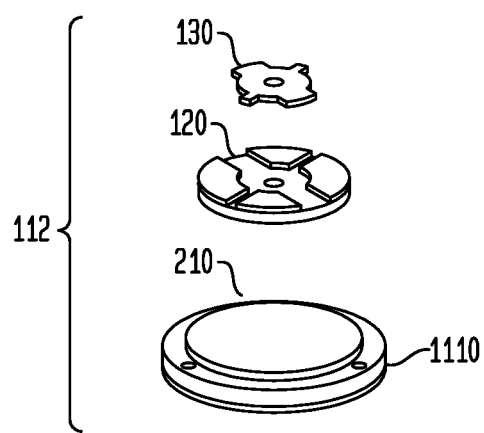
FIG. 12A illustrates an exploded perspective view of an exemplary PCB/LED assembly in accordance with a second aspect of the invention.

FIG. 12A illustrates an exploded perspective view of the positioning of the aperture holder 120 and aperture 130 onto PCB 210. As previously discussed, aperture holder 120 includes opening 125, which is sized to allow LED 115 to protrude therethrough such that a surface of LED 115 is substantially flush with a top surface of aperture holder 120. Opening 125 is sized and shaped to tightly accommodate LED 115, such that stray light from LED 115 is prevented from passing through. Aperture holder 120 furthermore centers aperture 130 on, or in close proximity to, LED 115 as previously discussed. Opening 135 in aperture 130 is sized to prevent stray light from LED 115 from passing through.

Figure 12B:
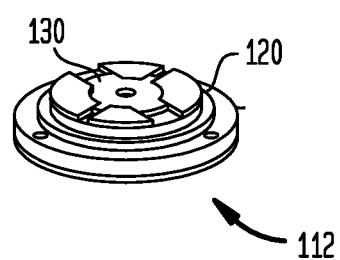
FIG. 12B illustrates a perspective assembled view of the exemplary PCB/LED assembly shown in FIG. 12A.

FIG. 12B illustrates a perspective view of an exemplary lighting element 112.

In this illustrated exemplary lighting element, aperture holder 120 is grooved or slotted to retain aperture 130 in place, wherein aperture 130 is constructed to match the grooves or slots within aperture holder 120. Although not shown, aperture 130 may include a plurality of tabs that engage a corresponding groove in aperture holder 120. The tabs on aperture 130 provide for an alignment of the aperture with the aperture holder 130 and LED 115.

Figure 12C:
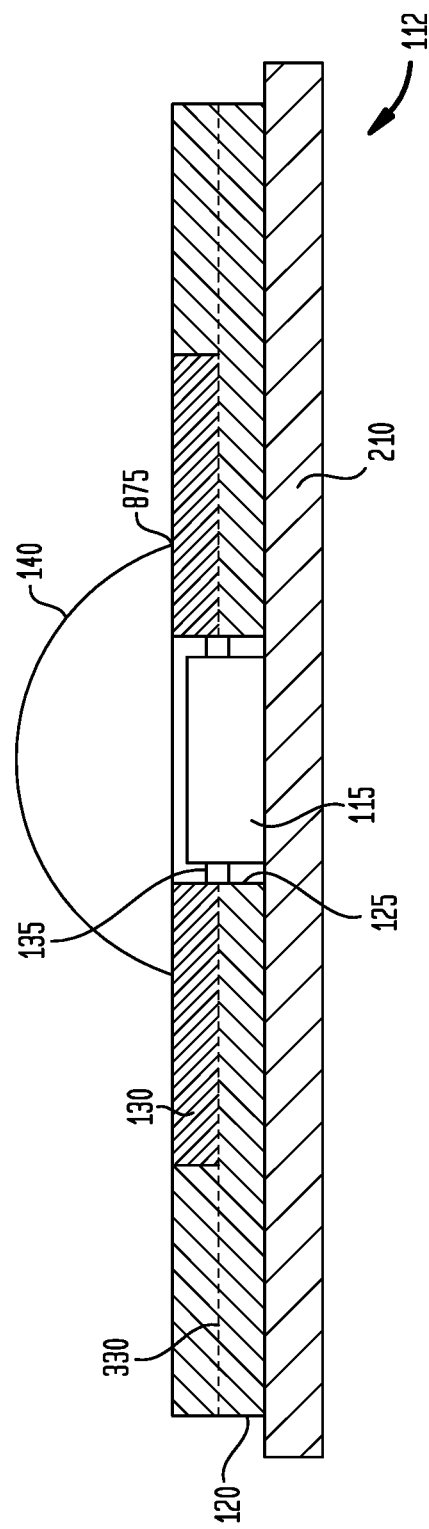
FIG. 12C illustrates a cross-sectional view of the exemplary PCB/LED assembly shown in FIG. 12B.

FIG. 12C illustrates a cross-sectional view of the assembled lighting element shown in FIG. 12B.

In this illustrated lighting element 112, aperture holder or aperture plate 120 is positioned atop PCB 210, wherein a portion of LED 115, on PCB 210, passes through passthrough 125, as previously discussed. Aperture holder 120 partially blocks light generated by the phosphorus section (border 114) of LED 115 from being visible. Further shown is aperture 130, contained within grooves or slots 330 of aperture plate 120. Aperture 130 includes passthrough 135, which allows light from LED 115 to passthrough. As discussed, with regard to FIGS. 3A-3C, passthrough 125 in aperture holder 120 and passthrough 135 in aperture 130 are sized to prevent stray light emitted from the phosphorus portion (block 114) of LED 115 to pass through. Thus, only a white light from LED 115 is passed to dome lens 140. Although white LED light is discussed, it would be recognized that the principles presented herein may be applied to LED light of different colors, without altering the scope of the invention.

Further, shown in FIG. 12C, is dome lens 140 positioned on a surface of aperture holder 120, as aperture 130 is contained entirely within groove 330. In an alternate embodiment, dome lens 140 may similarly be positioned on aperture 130 by sizing aperture 130 to be of a greater depth than groove 332 of aperture holder 120. In a further alternative embodiment, dome lens 140 may be positioned directly on LED 115 with the appropriate sizing of passthrough 135 in aperture 120. Further shown is optional anti-reflective coating 875. Anti-reflective coating 875 may be included on at least one of the rear surface of dome lens 140 and the domed surface of dome lens 140.

Returning to FIG. 8, incorporated onto a distal end of housing 110 is connector 820. Connector 820 provides means for attaching light assembly 100 onto a frame or eyewear (not shown). The frame may represent a means for retaining the light assembly to a person. The frame may be one of an eyewear, a headset, and a headband. Alternately, the frame may be a clip that may be used to attach the light assembly 100 to one of a shirt pocket, a belt, and shirt collar. Alternatively, the connector 820 may be used to position light assembly 100 in an overhead configuration or in a flashlight configuration.

In one aspect of the invention, connector 820 may include a slot 830 that allows for the removable attachment of light assembly 100 to the frame (not shown). The slot 830 may, for example, be a T-slot connector, which attaches to a mating T-slot connector on the frame (not shown).

Figure 13:
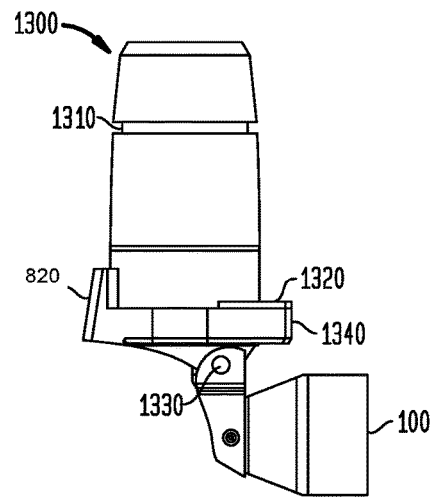
FIG. 13 illustrates an exemplary lighting unit including a light assembly shown in FIG. 8 in accordance with the principles of the invention.

FIG. 13 illustrates an exemplary lighting unit 1300 incorporating the light assembly 100 shown in FIG. 1, for example.

In this exemplary lighting unit 1300, light element 100 is attached though a pivot attachment 1330 to a housing section 1340, which includes an IR transmitter/detector system 1320. The IR transmitter/detector system may provide signals to the PCB 210 (not shown) of lighting element 112 to control the illumination output of LED 115.

Further illustrated is a battery pod element 1310, which includes a battery therein. The battery provides power (voltage/current) to the LED 115 of lighting element 112. The voltage/current provided by the battery to the LED 115 is controlled by one or more switches on PCB 210.

Battery pod 1310 may be attached to the housing section 1340 by one of a screw connection, a bayonet connection, a snap fit connection, etc.

Although the light assembly 100 is shown including a wireless or cordless operation of a switch to control a flow of electrical energy (i.e., power) to LED 115 (not shown), it would be recognized that light assembly 100 may include a physical switch that controls the flow of electrical energy to LED 115. For example, the switch may be a toggle switch that controls the application of power (i.e., voltage/current) to LED 115. Alternatively, the switch may be a capacitive touch switch that provides a signal to a switch that controls the application of power (i.e., voltage/current) to LED 115. For example, a capacitive touch switch may be activated when the battery pod 1310 is contacted, wherein a first touch may send a signal to the switch that allows power to be provided to LED 115 and a second touch sends a signal to the switch to prevent power from being provided to LED 115.

Figure 14:
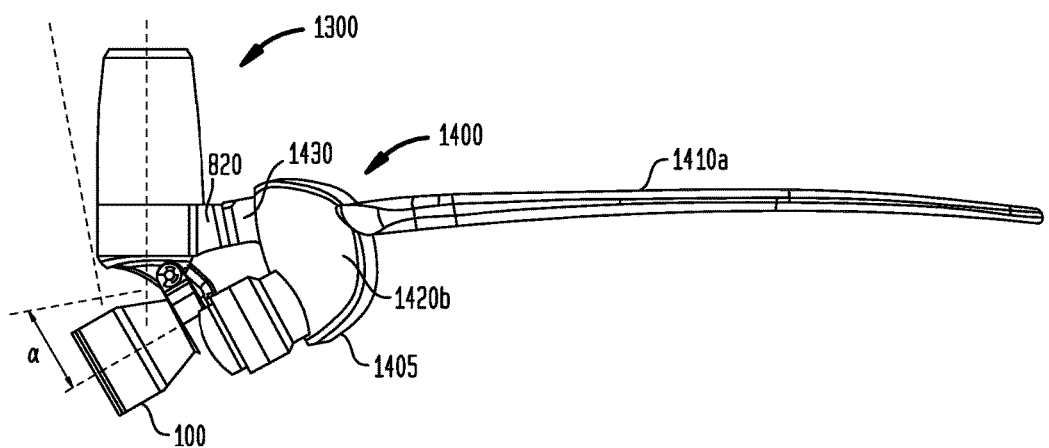
FIG. 14 illustrates an exemplary eyewear configuration incorporating the lighting unit shown in FIG. 13.

FIG. 14 illustrates an exemplary eyewear 1400 incorporating the lighting unit 1300 shown in FIG. 13. In this illustrative embodiment, lighting unit 1300 is attached, through connector 820, to eyewear 1400. Eyewear 1400 includes frame 1405 and lens 1420a (not shown) and 1420b. Further illustrated is temple 1410a that allows for the retention of eyewear 1400 to a person. As previously discussed, eyewear 1400 includes a connector 1430 matching the connector 820 to allow light unit 1300 to be removably attached to the eyewear 1400.

Although FIG. 14 illustrates a conventional eyewear 1400 through which lighting unit 1300 may be attached, it would be recognized that lighting unit 1300 may similarly be attachable to a headband, a headset, a shirt pocket, etc. Similarly, light assembly 100, and specifically the lighting element 112, may be incorporated into an overhead light, a desk lamp, etc., wherein a plurality of lighting elements may be concurrently used to provide for a large-scale light output.

Table 1 tabulates exemplary experimental results obtained from the lighting element configuration 112 illustrated in FIG. 7, in the light assembly 100 shown in FIG. 1, using the domed lens 140 of different chordal dissections in accordance with the principles of the invention.

In this exemplary test configuration, a light is projected onto a surface approximately sixteen (16) inches away (i.e., a known distance) from projection lens 152. The dome lens 140 is constructed from an exemplary 4 mm diameter sphere of optically transparent material (e.g., glass, crystal, optically clear plastic, etc.). A current applied to LED 115 is set at 700 milliamperes (mA). As would be known in the art, the current applied to LED 115 determines a light intensity produced by LED 115.

The selection of 700 milliamps is made merely to obtain the tabulated test results shown herein and is not considered the only current level that may be applied to LED 115.

Figure 15:
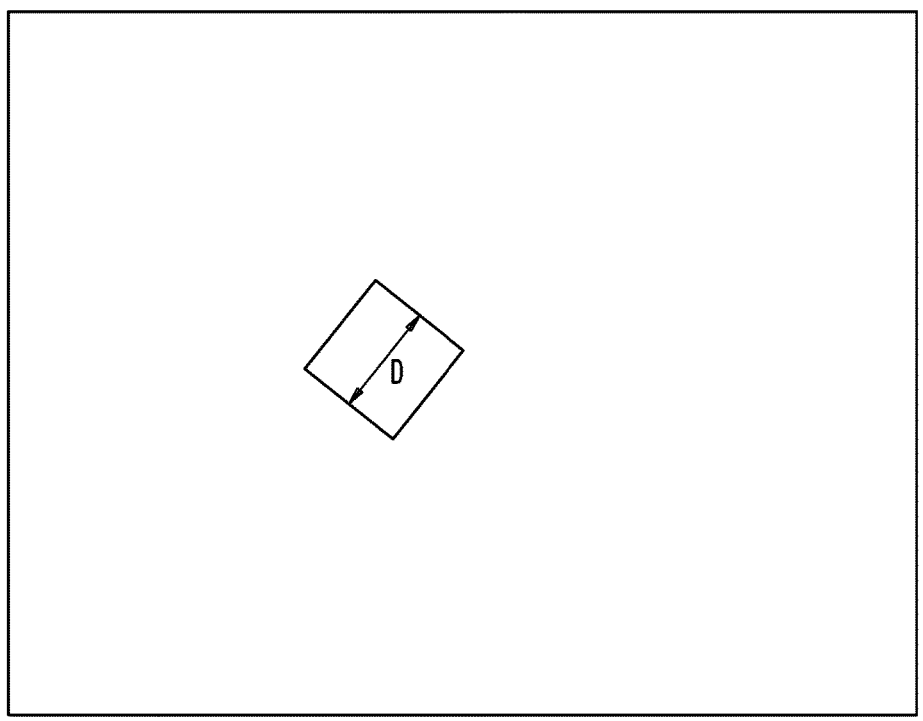
FIG. 15 illustrates an exemplary light projection in accordance with the principles of the invention.

FIG. 15 illustrates an exemplary light pattern projected onto the surface wherein the pattern is adjusted until a substantially square shape is displayed. In accordance with principles of the test, a dimension (D) of the projected square is set to be substantially the same for each of the different levels of magnification of dome lens 140.

A level of intensity of the projected light is measured, in foot-candles, for each of the different levels of magnification of dome lens 140 under the test conditions of the application of 700 ma of current, with a substantially same size projected light image (i.e., measurement D).

The Dome Lens Size (i.e., length) is defined as the distance between the chordal axis and an edge of the spherical dome. For example, the Dome Lens Size is represented by R, in FIG. 4B and R2 in FIG. 4E.

TABLE 1

| Dome Lens Size (height) (mm) | Lens Power (diopters) | Diagonal size (D) (mm) | Intensity (Foot-candles) |
| --- | --- | --- | --- |
| 2.00 | 26.5 × 2 lens | 45 | 6070 |
| 2.28 | 26.5 × 2 lens | 51 | 7500 |
| 2.41 | 21.5 × 2 lens | 46 | 7000 |
| 2.50 | 21.5 × 2 lens | 51 | 6800 |
| 2.70 | 21.5 × 2 lens | 59 | 6500 |
| 3.25 | 26.5 × lens | — | — |

In accordance with the principles of the invention, a dome lens 140, constructed from an exemplary 4 mm sphere, having characteristics that achieves a desired level of intensity and uniformity of light distribution over a desired size may be determined from the tabulated results.

Although Table 1 tabulates test results associated with a specific test condition (e.g., 4 mm sphere, 700 milliamp current), it would be understood that the results presented herein are only representations of the operation of the invention. Other chordal selections and/or sphere sizes and/or applied current values may be determined and have been contemplated and are considered to be within the scope of the invention claimed.

Figure 16:
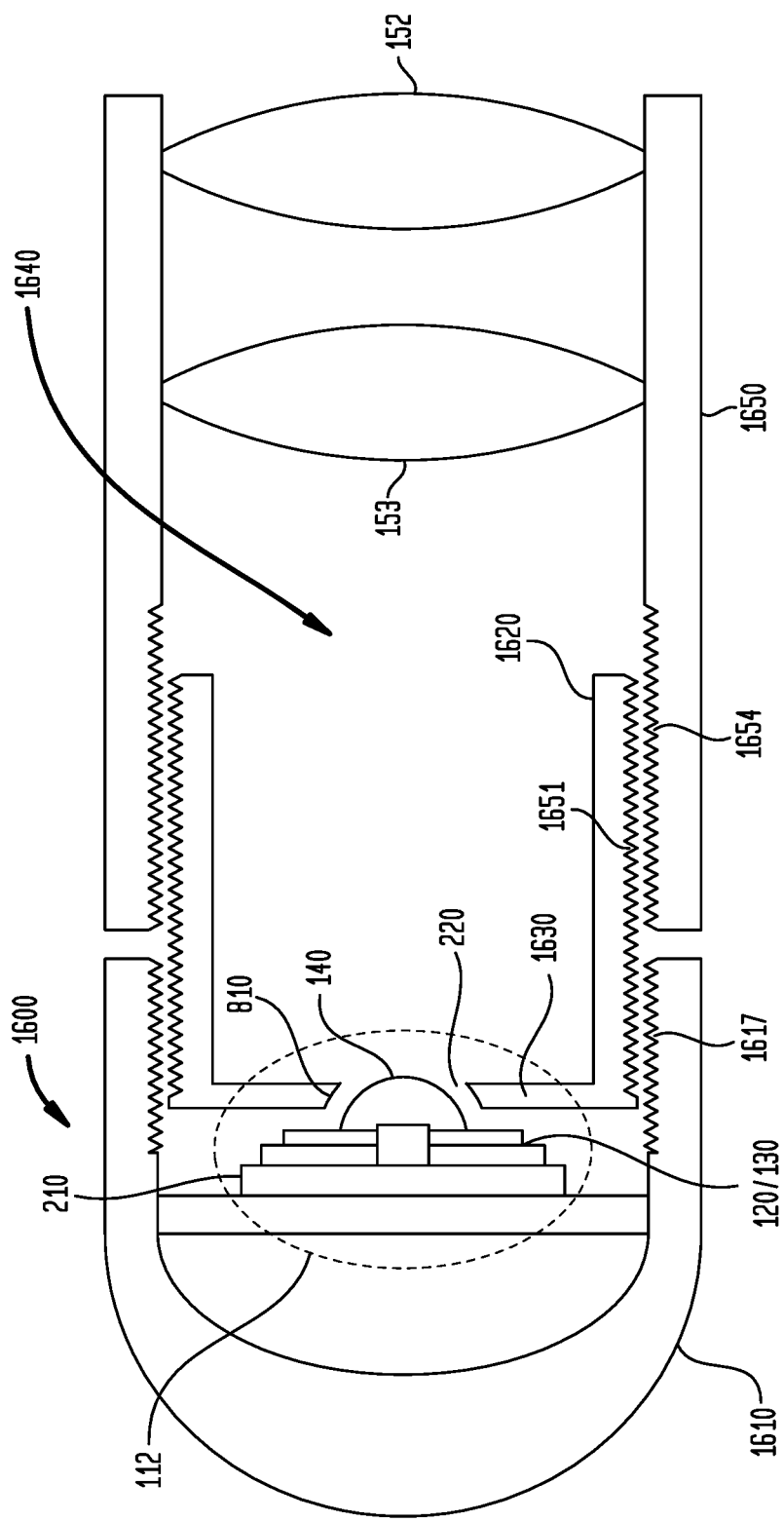
FIG. 16 illustrates a cross-sectional view of a second exemplary embodiment of the invention in accordance with the principles of the invention.

FIG. 16 illustrates a lighting element in accordance with a second exemplary embodiment of the invention claimed.

In this exemplary embodiment of light assembly 1600, which is similar to the light assembly shown in FIG. 1, including a housing 1610, into which is contained lighting element 112, including contained PCB 210, LED 115, aperture holder 120/aperture 130 and dome lens 140. Housing 1610 includes an internal screw thread 1617, which is similar to screw thread 117 contained in housing 110 shown in FIG. 1.

Further shown is lens assembly 1650 including lens 152, 153, which is similar to lens assembly 150 shown in FIG. 1. Further illustrated within lens assembly 1650 is internal screw thread 1654.

Further shown is coupler 1620, which includes a closed first end 1630, which is representative of retention means 215, and an open second end 1640. Closed first end 1630, similar to retention means 215, includes an opening 220, and surface 810 in opening 220, similar to those elements disclosed and shown with regard to FIG. 8 and FIGS. 10A-10C.

Coupler 1620 further includes a screw thread 1651 shown on an external surface of coupler 1620. Screw thread 1651, similar to the screw thread configuration disclosed with regard to screw thread 115 matches screw thread 1617 on inner surface of housing 1610.

In one aspect of the invention, screw thread 1651 may be positioned along an entire external surface of coupler 1620. In accordance with one aspect of the invention, screw threads 1651, 1654 and 1617 may be comparable with regard to thread count/inch and pitch. In another aspect of the invention, screw thread 1651 may be positioned along a portion of the external surface of coupler 1620, wherein screw threads 1654 and 1617 may be of a different thread count/inch and pitch and screw thread 1651 on coupler 1620 is formed to engage screw threads 1654 on one end and screw threads 1617 on a second end.

As previously discussed, surface 810, within retention means 215, is shaped (either conformally or tangentially) to contact a surface of dome lens 140 to retain dome lens 140 substantially in contact with (or in close proximity to) LED 115, without any adhesive materials.

In accordance with the principles of the invention, coupler 1620 may be screwed to housing 1610 through the connection of screw thread 1617 with screw thread 1615 to retain dome lens 140 in place, as previously discussed. Lens assembly 1650 may then be attached to coupler 1620 by the connection between screw thread 1651 and screw thread 1654.

Operation of the illustrated second embodiment of the light assembly 1600 is similar to that discussed with regard to FIG. 1, as heat generated by PCB 210/LED 115 may be channeled or drawn to the environment through the heat transfer from PCB 210 through coupler 1620 and lens assembly 1650.

Although FIGS. 1 and 16 illustrate coupler 1620 including retention means 215, including a screw thread for attaching the lens assembly 150 (or 1650) to housing 110 (1610), it would be recognized that attachment means 225 (coupler 1620) may include a bayonet connection, a snap fit connection, or a butt fit connection without altering the scope of the invention.

The illustrated second embodiment of the invention shown in FIG. 16 allows for the changing of lens assembly 1650 (and the projection lens 152, 153) without causing any change in the position of dome lens 140 held in place by surface 810.

Figure 17:
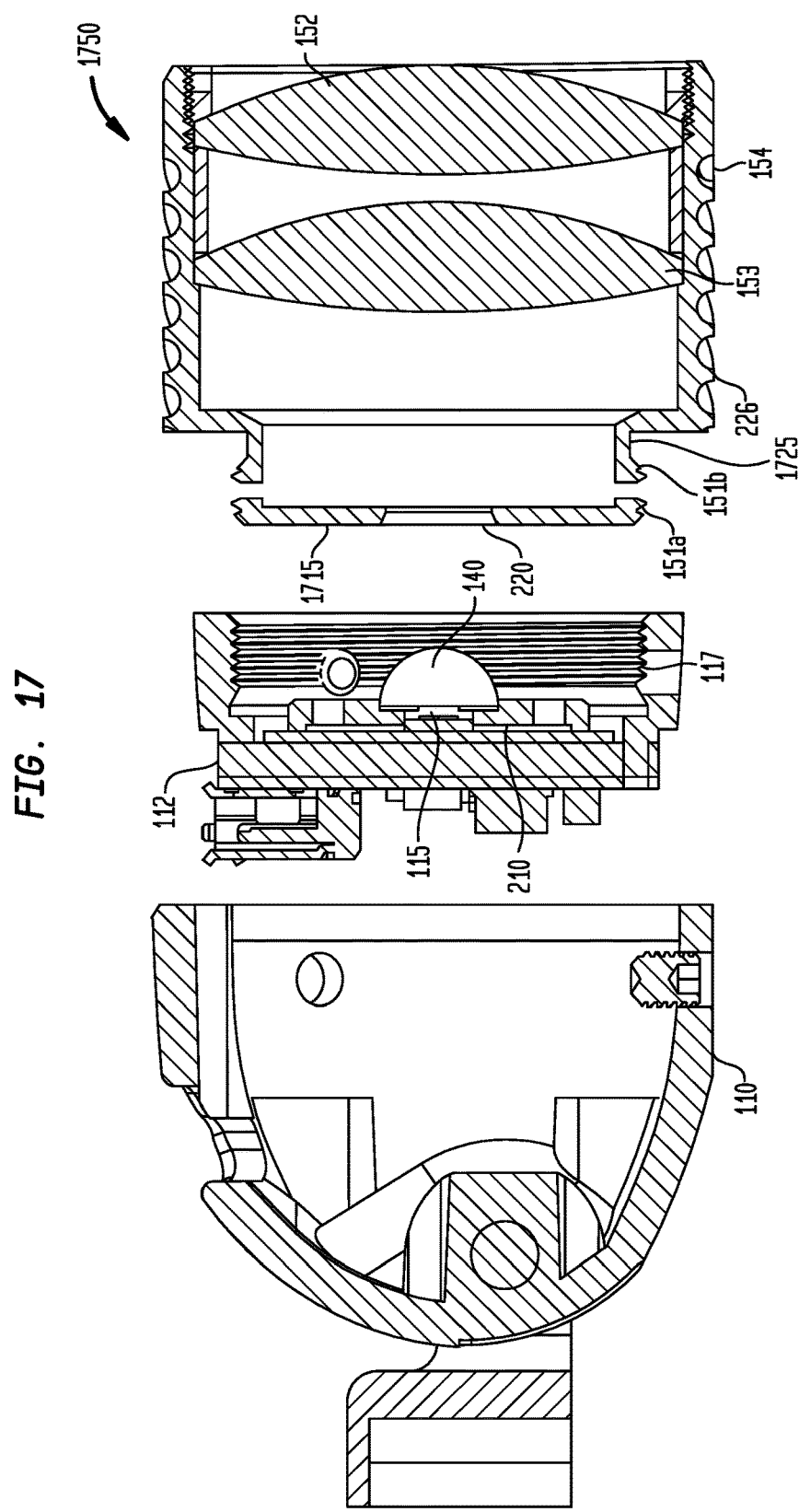
FIG. 17 illustrates a cross-sectional view of a third exemplary embodiment of the invention in accordance with the principles of the invention.

FIG. 17 illustrates a cross-sectional view of a third exemplary embodiment of the invention in accordance with the principles of the invention.

FIG. 17, similar to FIG. 2, illustrates a housing 110, a lighting element 112 and lens housing 1750 containing at least one lens 152, 153. As housing 110 and lighting element 112 are comparable to these elements discussed with regard to FIG. 2, a detailed discussion of these elements need not be repeated.

In this exemplary embodiment, lens housing 1750 is comparable to lens housing 150, discussed with regard to FIG. 2, in that lens housing 1750 includes a lens section 226 and an attachment section 1725. Attachment section 1725 further includes threads 151b, similar to threads 151 shown in FIG. 2. Threads 151b operate in a manner similar to threads 151, of FIG. 2, in attaching lens assembly 1750 to housing 110.

In this illustrated third embodiment, attachment section 1725 of lens assembly 1750 is open ended, wherein light generated from LED 115 passes through to at least one lens 152, 153.

Further illustrated is attachment plate 1715 (i.e., retainer 215), which including threads 151a and passthrough 220. Threads 151a, similar to threads 151, engage threads 117 in housing 110 to allow attachment plate 1715 (retainer 215) to engage dome lens 140.

Passthrough 220 includes surface 810 that was disclosed with regard to FIG. 8.

In accordance with the principles of the invention, threads 151a on attachment plate 1715 engage threads 117 until surface 810 engages dome lens 140. Threads 151b on attachment section 1725 may similarly engage threads 117 to retain lens assembly and housing 110 together.

As previously discussed, heat generated by LED 115/PCB 210 is transferred through attachment plate 1715 and attachments section 1725 to be dispersed to the environment by lens assembly 1750.

In summary, a lighting element for providing a brighter light output using new generation LEDs is disclosed. By incorporating an LED within or at the focal length of the dome lens that is placed on or in close proximity to the LED without glue or adhesive, the LED light output is focused (or de-focused) and concentrated onto a projection lens. Further disclosed is a light assembly including a housing incorporating the lighting element therein and a lens assembly, that is constructed to attach to the housing and concurrently retaining the dome lens on or in close proximity to the LED without glue or adhesive. In accordance with the principles of the invention, the LED is positioned within a focal length of a projection lens within the lens assembly. By defocusing the LED light output, using both a close dome lens and a far-away projection lens, a brighter and more defined, substantially uniform, light output is achieved. Also disclosed is a method for mounting the dome lens onto the LED to satisfy the positional relationship between the LED and the dome lens.

Although the present invention has been described about an eyeglass configuration, it would be recognized that the lighting element 112 (assembly 100) described herein may be applied to other types of headwear configurations. For example, a headband including one or more lens or a monocular assembly (which are referred to herein as eyewear) may incorporate the lighting element 112 (assembly 100) described herein. Furthermore, although a user wearable device is discussed, it would be appreciated that the principles of the invention may be applied to other types of lighting sources. For example, overhead lighting sources, flashlights, etc., incorporating a lighting element 112 (assembly 100) in accordance with the principles of the invention have been contemplated and within the scope of the invention claimed. Although an LED type light is contemplated and discussed with the lighting element 112 described herein, it would be recognized that other types of lighting sources may be utilized without altering the scope of the invention claimed.

The invention has been described with reference to specific embodiments. One of ordinary skill in the art, however, would recognize that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above about specific embodiments. The benefits, advantages, and solutions to problems, and any element(s) that may cause any benefits, advantages, or solutions to occur or become more pronounced, are not to be construed as a critical, required, or an essential feature or element of any or all the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A lighting assembly comprising:
   a lens assembly comprising:
      at least one projection lens,
   a housing comprising:
      a lighting element comprising:
         a printed circuit board;
         a Light Emitting Diode (LED) positioned on the printed circuit board;
      an aperture plate comprising:
         a first groove positioned along a diameter of the aperture plate; and
         a second groove, substantially perpendicular to the first groove, positioned along a diameter of the aperture place; and
         a first passthrough positioned at an intersection of the first groove and the second groove, said first passthrough sized to allow a center portion of the LED to be viewed therethrough;
      an aperture comprising:
         a first leg; and
         a second leg substantially perpendicular to the first leg, and
         an aperture passthrough positioned at an intersection of the first leg and the second leg, said aperture passthrough sized to allow a center section of the LED to be viewed therethrough, said aperture configured to be positioned within the first groove and the second groove of the aperture plate;
      a dome lens, proximate to the LED, wherein a position of the LED is one of: at a focal length of the dome lens and within a focal length of the dome lens;
      a retainer configured to:
         contact the dome lens soley along a curved surface of the dome lens to retain the dome lens proximate to the LED; and
      an attachment section configured to:
         attach the lens assembly to the housing.

2. The lighting assembly of claim 1, wherein the retainer comprising:
   a first surface;
   an opposing second surface, and
   a retainer passthrough extending between the first surface and the opposing second surface, said retainer passthrough comprising:
      a retainer passthrough surface configured to contact the curved surface of said dome lens.

3. The lighting assembly of claim 2, wherein the retainer passthrough surface is one of: substantially conformal and substantially tangential to the curved surface of the dome lens.

4. The lighting assembly of claim 1, wherein the attachment section comprises one of: a screw thread, a bayonet connection, a snap fit connection and a butt fit connection.

5. The lighting assembly of claim 1, wherein the attachment section is integral to the lens assembly.

6. The lighting assembly of claim 1, wherein the attachment section is a coupler.

7. The lighting assembly of claim 1 wherein the LED is positioned within a focal length of said at least one projection lens.

8. The lighting assembly of claim 1, wherein the dome lens comprises:
   a spherical cap constructed from a sphere cut along a chordal plane.

9. The lighting assembly of claim 1, wherein the dome lens comprises:
   a spherical cap fabricated into a desired shape.

10. The lighting assembly of claim 1, wherein the lens assembly comprises:
   at least one deformation on an outer surface of the lens assembly.

11. The lighting assembly of claim 10, wherein the at least one deformation comprises one of: a groove and a protrusion.

12. The lighting assembly of claim 1, wherein the printed circuit board comprises:
   a switch configured to:
      apply an electrical energy to the LED.

13. The lighting assembly of claim 1, wherein the lighting element further comprises:
   a ring assembly containing the PCB therein, said ring assembly in physical contact with at least one of: the housing and the attachment section.

14. The lighting assembly of claim 1, further comprising:
   an anti-reflective layer on at least one surface of the dome lens.

15. The lighting assembly of claim 13, further comprising:
   a threaded ring in contact with said ring assembly.

16. The lighting assembly of claim 15, wherein said attachment section comprises a threaded section configured to engage said threaded ring.

17. A lighting assembly comprising:
   a housing;
   a lighting element, positioned within the housing, comprising:
      a substrate; comprising:
         a printed circuit board containing electronic components thereon;
         a Light Emitting Diode (LED) electrically connected to the printed circuit board;
      an aperture holder positioned on the printed circuit board, the aperture holder comprising:
         at least a first depression along a diameter of the aperture holder; and
         a second depression, along a diameter of the aperture holder, substantially perpendicular to the first depression; and
         an aperture holder opening positioned at an intersection of the first depression and the second depression, the opening sized to allow a center portion of the LED to be viewable; and
         an aperture positioned within the first depression and the second depression of the aperture holder, the aperture including an opening no greater in size that a size of the aperture holder opening;
         a dome lens positioned proximal to the aperture holder opening, wherein the LED is positioned at or within a focal length of the dome lens, and
      a ring element positioned along a perimeter of the substrate;
      a retainer comprising:
         a first surface in contact with said ring element;
         a second surface opposing said first surface; and
         a retainer passthrough extending between the first surface and the second surface, said retainer passthrough configured to:
         contact said dome lens, solely along a curved surface of the dome lens, wherein said contact to the dome lens is one of: substantially conformal and substantially tangential to said curved surface of the dome lens;
      a lens assembly comprising:
         at least one lens; and
         a connector configured to:
         attach the lens assembly to the housing.

18. The light assembly of claim 17, further comprising:
   an anti-reflective layer on at least one surface of the dome lens.

19. The light assembly of claim 17, wherein the retainer is one of: attached to the lens assembly and separate from the lens assembly.

* * * * *

UNITED STATES PATENT AND TRADEMARK OFFICE
CERTIFICATE OF CORRECTION

PATENT NO. : 10,247,384 B1
APPLICATION NO. : 15/921217
DATED : April 2, 2019
INVENTOR(S) : Richard E. Feinbloom, Kenneth N. Braganca and Matthew Kenyon Page 1 of 1

It is certified that error appears in the above-identified patent and that said Letters Patent is hereby corrected as shown below:

In the Claims

Column 21, Line 40 Claim 17 delete ";"

Signed and Sealed this
Twenty-fourth Day of September, 2019

Andrei Iancu
*Director of the United States Patent and Trademark Office*